US010551392B2

United States Patent
Lao-Sirieix et al.

(10) Patent No.: US 10,551,392 B2
(45) Date of Patent: *Feb. 4, 2020

(54) BIOMARKER FOR BARRETT'S OESOPHAGUS

(71) Applicant: Medical Research Council, London (GB)

(72) Inventors: Pierre Lao-Sirieix, Cambridge (GB); Rebecca C. Fitzgerald, Cambridge (GB)

(73) Assignee: Covidien LP, Mansfield, MA (US)

( * ) Notice: Subject to any disclaimer, the term of this patent is extended or adjusted under 35 U.S.C. 154(b) by 32 days.

This patent is subject to a terminal disclaimer.

(21) Appl. No.: 15/465,298

(22) Filed: Mar. 21, 2017

(65) Prior Publication Data

US 2018/0074075 A1     Mar. 15, 2018

Related U.S. Application Data

(63) Continuation of application No. 14/175,737, filed on Feb. 7, 2014, now Pat. No. 9,632,099, which is a continuation of application No. 12/833,548, filed on Jul. 9, 2010, now Pat. No. 8,709,736.

(51) Int. Cl.
| | |
|---|---|
| *C12Q 1/24* | (2006.01) |
| *G01N 33/68* | (2006.01) |
| *G01N 21/75* | (2006.01) |
| *G01N 33/574* | (2006.01) |

(52) U.S. Cl.
CPC .......... *G01N 33/6893* (2013.01); *C12Q 1/24* (2013.01); *G01N 21/75* (2013.01); *G01N 33/57446* (2013.01); *G01N 2333/4725* (2013.01); *G01N 2800/14* (2013.01)

(58) Field of Classification Search
CPC ............... G01N 33/6893; G01N 21/75; G01N 33/57446; G01N 2333/4725; G01N 2800/14; C12Q 1/24
See application file for complete search history.

(56) References Cited

U.S. PATENT DOCUMENTS

| | | | | |
|---|---|---|---|---|
| 8,709,736 | B2 * | 4/2014 | Lao-Sirieix | ...... G01N 33/57446 435/7.21 |
| 9,632,099 | B2 * | 4/2017 | Lao-Sirieix | ...... G01N 33/57446 |

OTHER PUBLICATIONS

Lao-Sirieix et al. Non-endoscopic screening for Barrett's Esophagus Using the Capsule Sponge is Well Tolerated and a Newly Applied Clot Processing Method Allows Tissue Architecture to be Retained. J. Clin. Gastroenterol. 42 (Supp.1): S28: 157 (Apr. 2008).*
Kadri et al. Development of Biomarkers for non-endoscopic screening for Barrett's Esophagus. Gastroenterology AGA Abstracts A-593: T1887 (May 2009).*
DeMeester et al. (Columnar Mucosa and Intestinal Metaplasia of the Esophagus. Annals of Surgery. 231(3); 303-321 (2000)).*
Avgeris, Margaritas, et al., "Expression analysis and clinical utlity of L-Dopa decarboxylas (DDC) in prostate cancer," Clinical Biochemistry, 41 (2008) 1140-1149.

(Continued)

*Primary Examiner* — Gailene Gabel
(74) *Attorney, Agent, or Firm* — Holland & Hart LLP

(57) ABSTRACT

The present invention, relates to the use of TFF3 in the diagnosis and detection of Barrett's Oesophagus using non-invasive, non-endoscopic methods.

18 Claims, 11 Drawing Sheets

Specification includes a Sequence Listing.

(56) References Cited

OTHER PUBLICATIONS

Barbiere, Josephine M., et al., "Cost-Effectiveness of Endoscopic Screening Followed by Surveillance for Barrett's Esophagus: A Review," Gastroenterology 2009; 137:1869-1876.
Baus-Loncar, M., et al., "Trefoil factor family 2 deficiency and immune response," Cellular and Molecular Life Sciences, 62 (2005) 2947-2955.
Watson, A., et al., Guidelines for the Dianosis and Management of Barrett's columnar-lined Oesophagus, A Report of the Working Part of the British Society of Gastroenterology, Aug. 2005, http://www.bsg.org.uk, obtained Sep. 23, 2013.
Jin et al., Cancer Res., 69(10):4112-4115 (2009).
Lao-Sirieix et al., Clin. Cancer Res., 13(2 Pt 1):659-665 (2007).
Murray et al., Gut., 55(10): 1390-01397 (2006).
Paik et al., J. Clin. Oncol., 24(23):3726-3734 (2006).
Paik et al., N. Engl. J. Med., 351(27):2817-2826 (2004).
Sakakura et al., Br. J. Cancer, 90(3):665-671 (2004).
Schlemper et al., Gut., 47(2):251-255 (2000).
Schulmann et al., Oncogene, 24(25):4138-4148 (2005).
Shaheen et al., N. Engl. J. Med., 360(22):2277-2288 (2009).
Sirieix et al., clin. Cancer Res., 9(7):2560-2566 (2003).
Towler et al., BMJ, 317(7158):559-565 (1998).
Bunting, Peter S., "Screening for Prostate Cancer with Prostate-Specific Antigen: Beware the Biases," Clinica Chimica Acta 315 (2002) 71-97.
Chandrasoma, P., et al., "Is Intestinal Metaplasia a Necessary Precursor lesion for adenocarcinomas of the distal esophagus, gastroesophageal junction and gastric cardia?" Diseases of the Esophagus (2007) 20, 36-41.
Corley, Douglas A., "Surveillance and Survival in barrett's Adenocardinomas: A Population-Based Study," Gastroenterology, 2002; 122:633-640.
Donaldson, L., On the State of Public Health: Annual Report of the Chief Medical Officer 2007, Department of Health, 086176: Accessed Jan. 20, 2009; http://www.dh.gov.uk/enPublicationsandstatistics/PublicationsAnnualReports/DH_086176:Accessed Jan. 20, 2009.
Donaldson, L., "A Pathological concern: Understanding the Rise in Oesophageal Cancer," Cahpter 6, (2007) Annual Report of the Chief Medical Officer, http://www.dh.gov.uk/en/Publicationsandstatistics/Publications?AnnualReports/DH086176.
Dumortier, Jerome, et al., "Unsedated Transnasal EGD in Daily Practice: Results with 1100 consecutive Patients," Gastrointestinal Endoscopy, vol. 57, No. 2, 2003: 198-204.
Eldrup, E, et al., "Evaluation of Plasma 3, 4-dihydroxphenylacetic acid (DOPAC) and plasma 3, dihydroxyphenylalanine (DOPA) as tumor markers in children with neuroblastoma," Scand J Clin Lab invest, 2001;61:479-490.
Falk, Gary W., et al. "Surveillance of Patients with Barrett's Esophagus for Dysplasia and Cancer with balloon Cytology," Gastroenterology, 1997; 112:1787-1797.
Fang, Ming, et al., "DNA Abnormalities as Marker of Risk for Progression of Barrett's Esophagus to Adenocarcinoma: Image Cytometric DNA Analysis in Formlin-Fixed Tissues," American Journal Gastroenterology, (Am J Gastroenterol 2004;99:1887-1894).
Fennerty, M. Brian, et al., "Screening for Barrett's Esophagus by Balloon Cytology," The American Journal of Gastroenterology, vol. 90, No. 8, 1995:1230-1232.
Ferguson, Mark K., et al., "Long-term Survival After Esophagectomy for Barrett's Adenocarcinoma in Endoscopically Surveyed and Nonsurveyed Patients," Journal of Gastrointestinal Surgery, PII: 51091-255X (01)00052-X:29-35, (2002).
Fountoulakis, A., et al., "Effect of Surveillance of Barrett's Oesophagus on the clinical Outcome of Oesophageal Cancer," British Journal of Surgery 2004; 91-:997-1003.
Gerson, Lauren B., et al., "Use of A Simple Symptom Questionnaire to Predict Barrett's Esophagus in Patients with Symptoms of Gastroesophageal Reflux," The american Journal of Gastroenterology, vol. 96, No. 7, 2001:2005-2012.
Gerson, Lauren B., et al., "Prevalence of Barrett's Esophagus in Asymptomatic Individuals," Gastroenterology 2002;123:461-467.
Greenawalt, Danielle M., "Gene Expression profiling of Esophageal Cancer: Comparative Analysis of Barrett's Esophagus, Adenocarcinoma, and squamous cell carcinoma," Int. J. Cancer: 120, 1914-1921 (2007).
Hoffmann, W., et al., "Molecular medicine of TFF-peptides: from gut to brain," Hisotology and Histopathology (2001) 16:319-334.
Ilyas, Sumera, et al., "Chemoprevention in Barrett's Esophagus," Journal Gastrointest Canc (2007) 38:1-9.
Incarbone, R., et al., "Outcome of esophageal adenocarcinoma detected during endoscopic biopsy surveillance for Barrett's esophagus," Surgical Endoscopy (2002) 16: 263-266.
Jones, R., et al., "The Gastro-oesophageal Reflux Disease Impact Scale: a patient management tool for primary care," Alimentary Pharmacology & therapeutics, (2007) 25, 1451-1459.
Kadri, Sudarshan R., et al. "Development of Biomarkers for Non-Endoscopic Screening for Barrett's Esophagus," AGA Abstracts, 136(Suppl 1): T1877 (2009).
Kadri, Sudarshan R., et al., "A prospective, Multicenter Study to Evaluate a Novel, Nonendoscopic screening Device for Barrett's Esophagus in the Community Setting," Gastroenterology 2010; 139:e17-e19.
Kouznetsova, Irina, et al., "Localization of TFF3 peptide in human esophageal submucosal glands and gastric cardia: differentiation of two types of gastric pit cells along the rostro-caudal axis," Cell Tissue Res (2007) 328:365-374.
Lao-Sirieix P., et al., "Non-endoscopic screening biomarkers for Barrett's oesophagus: from microarray analysis to the clinic," Oesophagus, Gut 2009;58:1451-1459.doi:10.1136/gut.2009.180281.
Lao-Sirieix, Pierre, et al., "Non-endoscopic immunocytological screening test for Barrett's oesophagus," Gut., 56 (7): 1033-1034 (2007).
Lao-Sirieix, et al., "Nonendoscopic Screening for Barrett's Esophagus Using the Capsule Sponge is Well Tolerated and a Newly applied Clot Processing Method Allows tissue architecture to be Retained," J. Clin. Gastroenterol, vol. 42, Supp. 1, Apr. 2008.
Lepage, Come, et al., Continuing Rapid Increase in Esophageal Adenocarcinoma in England and Wales, American Journal of Gastroenterology, 103(11):2694-2699 (2008).
Locke, G. Richards, et al., "A New questionnaire for Gastroesophageal Reflux Disease," Mayo Clin Proc. 1994; 60:539-547).
Lancet, "Surgical resection with or without preoperative chemotherapy in oesophageal cancer: a randomized controlled trial," Lancet 2002; 359:1727-33.
Mehta, S., et al., "Systematic Review: The Chemoprevention of Oesophageal adenocarcinoma," Aliment Pharmacol Ther 2005; 22:759-768.
Nanda, Kavita, et al., "Accuracy of the Papanicolaou Test in Screening for an Follow-up of Cervical Cytologic Abnormalities: A Systematic Review," Ann Intern Med. 2000; 132:810-819.
National Institute for Health and clinical Excellence (NICE), "Guide to the Methods of Technology Appraisal," (2008) http://www.nice.org.uk/media/4A6/of/SelectedFurtherReading21_0708.
Peitz, Ulrich, et al., "TFF3 expression at the esophagogastric junction is increased in gastro-esophageal reflex lisease (GERD)," Peptides 25 (2004) 771-777.
Pera, Manual, "Trends in Incidence and Prevalence of Specialized Intestinal Metaplasia, Barrett's Esophagus, and Adenocarcinoma of the Gastroesophageal Junction," World J. Surg. 27, 999-1008, 2003.
Peters, Jeffery H., et al., "Outcome of adenocarcinoma arising in Barrett's esophagus in endoscopically surveyed and nonsurveyed patients," The Journal of Thoracic and Cardiovascular Surgery, www.jtcvsonline.org/article/PIIS0022522394701784/fulltext; obtained Sep. 23, 2013.
Pouw, Roos E., et al., "Efficacy of Radiofrequency Ablation Combined with Endoscopic resection for Barrett's Esophagus with Early Neoplasia," Clinical Gastroenterology and Hepatology, 2010;8:23-29.
Ramirez, Francisco C., et al., "Screening of Barrett's Esophagus with String-Capsule Endoscopy: A prospective blinded study of 100

(56) References Cited

OTHER PUBLICATIONS consecutive patients using histology as the criterion standard," vol. 68, No. 1: 2008, Gastrointestinal Endoscopy, p. 25-31.
Reddymasu, Savio C., "Advances in Endoscopic Imaging of the Esophagus," Gastroenterol Clin. N. Am. 37 (2008) 763-774.
Rex, Douglas K., et al., "Screening for Barrett's Esophagus in Colonoscopy Patients with and Without Heartburn," Gastroenterology, 2003;125:1670-1677.
Ronkainen, Jukka, et al., "Prevalence of Barrett's Esophagus in the General Population: An Endoscopic Study," Gastroenterology 2005; 129:1825-1831.
Saeian, Kia, et al., "Unsedated transnasal endoscopy accurately detects Barrett's mataplasia and dysplasia," Gastrointestinal Endoscopy, vol. 56, No. 4, 2002.
Schlansky, B., et al., "A Survey of Oesophageal Cancer: Pathology, Stage and Clinical Presentation," Alimentary Pharmacology & Therapeutics, 23, 587-593, (2006).
Sharma, Prateek, et al., "The Diagnostic Accuracy of Esopageal Capsule Endoscopy in Patients with Gastroesophageal Reflux Disease and Barrett's Esophagus: A Blinded, Prospective Study," American Journal of Gastroenterology 2008; 103:525-532.
Shimada, Tadahito, et al., "Regulation of TFF3 expression by homeodomain prtein CDX2," Regulatory Peptides 140 (2007) 81-87.
Sikkema, Marjolein, et al., "Risk of Esophageal Adenocarcinoma and Martality in Patients with Barrett's Esophagus: A Systematic Review and Meta-Analysis," Clinical Gastroenterology and Hepatology 2010;8:235-244.
Spechler, Stuart Jon, "Barrett's Esophagus: Should We Brush Off this Ballooning Problem?" Gastroenterology 1997; 112:2138-2152.
Streitz, John et al., "Endoscopic Surveillance of Barrett's esophagus," The Journal of Thoracic and Cardiovascular Surgery, vol. 105, No. 3, Mar. 1993.
Takano, Toru, et al., "Trefoil Factor 3 (TFF3): A Promising Indicator for Diagnosing Thyroid Follicular Carcinoma," Endocrine Journal 2009, 56 (1), 9-16.
Theisen, J., et al., "Preoperative chemotherapy unmasks underlying Barrett's mucosa in patients with adenocarcinoma of the distal esophagus," Surgical Endoscopy and Other Interventional Techniques, 2002 16: 671-673.
Trager, Catarina, et al., "mRNAs of Tyrosine hydroxylase and dopa decarboxylase but not of GD2 Synthase are specific for neurblastoma minimal disease and preducts outcome for children with high-risk disease when measure at diagnosis," Int. J. Cancer:123, 2849-2855 (2008).
UK National Screening Committee, "Criteria for Appraising the Viability, Effectiveness and Appropriateness of a Screening Protramme," (2009) http://www.screening.nhs.uk/criteria. Obtained Sep. 23, 2013.
Van Baal, Jantine W. P.M., et al., "A Comparative Analysis by SAGE of Gene Expression Profiles of Barrett's Esophagus, Normal Squamous Esophagus, and Gastric Cardia," Gastroenterology 2005; 129:1274-1281.
Veer, Laura J. van't, et al., "Gene Expression Profiling Predicts Clinical Outcome of Breast Cancer," Nature, vol. 415, Jan. 31, 2002.
Wang, et al., "Updated Guidelines 2008 for Diagnosis, Surveillance and Therapy of Barrett's Esophagus," Updated Guidelines 2008 for the Diagnosis, Surveillance and Therapy of Barrett's Esophagus, American Journal of Gastroenterology, 2008; 103:788-797.
Ward, Eric M. et al., "Barrett's Esophagus is Common in Older Men and Women Undergoing Screening Colonoscopy Regardless of Reflux Symptoms," American Journal of Gastroenterology, 2006; 101:12-17.
Bignotti et al., Br. J. Cancer, 99(5):768-773 (2008).
Boussioutas et al., Cancer Res., 63(10):2569-2577 (2003).
Brown et al., J. Natl. Cancer Inst, 100(16):1184-1187 (2008).
Bryson, et al., Arch Otolaryngol. Head Neck Surg., 134(6):581-586 (2008).
Chao et al., Clin. Cancer Res., 14(21):6988-6995 (2008).
Christenson et al., Proc. Natl. Acad. Sci. USA, 69(2):343-347 (1972).
Dignass et al., J. Clin. Invest., 94(1):376-383 (1994).
Galipeau et al., PLoS Med., 4(2):e67 (2007).
Gilbert et al., Am. J. Pathol., 155(1):17-21 (1999).
Hao et al., Gastroenterology, 131(3):925-933 (2006).
Jensen et al., Cancer Res., 50(18):6068-6074 (1990).
Dunn, J. M., et al., "Comparison of Image Cytometry and Flow Cytometry for Detection of DNA Ploidy Abnormalities in Barrett's Oesophagus," 2009 Biochemical Society Transactions.

* cited by examiner

|  | Number | Year 1 ||||||||||||
|---|---|---|---|---|---|---|---|---|---|---|---|---|---|
|  |  | Month 1 | Month 2 | Month 3 | Month 4 | Month 5 | Month 6 | Month 7 | Month 8 | Month 9 | Month 10 | Month 11 | Month 12 |
| Screening trial: Primary care | | | | | | | | | | | | | |
| Set up period + ethics | | | | | | | | | | | | | |
| Recruitment surgeries | 25 | | | | | | | | | | | | |
| Cytopill clinics: first swallow | 1000 | | | | | | | | | | | | |
| Cytopill clinics: Repeat | 100 | | | | | | | | | | | | |
| Sample processing and analysis | | | | | | | | | | | | | |
| Endoscopy | 115 | | | | | | | | | | | | |
| Data analysis | | | | | | | | | | | interim | | |
| | | | | | | | | | | | | | |
| Case-control study: Secondary care | | | | | | | | | | | | | |
| Set up period + ethics | | | | | | | | | | | | | |
| Cytopill: Barrett's cases first swallow | 150 | | | | | | | | | | | | |
| Cytopill: Barrett's cases follow up | 40 | | | | | | | | | | | | |
| Cytopill: dyspeptic controls | 200 | | | | | | | | | | | | |
| Sample processing and analysis | | | | | | | | | | | | | |
| Data Analysis | | | | | | | | | | interim | | | |

FIG. 9A

|  | Number | Year 2 | | | | | | | | | | | |
| --- | --- | --- | --- | --- | --- | --- | --- | --- | --- | --- | --- | --- | --- |
|  |  | Month 13 | Month 14 | Month 15 | Month 16 | Month 17 | Month 18 | Month 19 | Month 20 | Month 21 | Month 22 | Month 23 | Month 24 |
| Screening trial: Primary care | | | | | | | | | | | | | |
| Set up period + ethics | | | | | | | | | | | | | |
| Recruitment surgeries | 30 | | | | | | | | | | | | |
| Cytopill clinics: first swallow | 1250 | | | | | | | | | | | | |
| Cytopill clinics: Repeat | 500 | | | | | | | | | | | | |
| Sample processing and analysis | | | | | | | | | | | | | |
| Endoscopy | 139 | | | | | | | | | | | | |
| Data analysis | | | | | | | | | | interim | | | |
| | | | | | | | | | | | | | |
| Case-control study: Secondary care | | | | | | | | | | | | | |
| Set up period + ethics | | | | | | | | | | | | | |
| Cytopill: Barrett's cases first swallow | 250 | | | | | | | | | | | | |
| Cytopill: Barrett's cases follow up | 120 | | | | | | | | | | | | |
| Cytopill: dyspeptic controls | 200 | | | | | | | | | | | | |
| Sample processing and analysis | | | | | | | | | | | | | |
| Data Analysis | | | | | | | | | | interim | | | |

FIG. 9B

|  | Number | Year 3 | | | | | | | | | | | Total number |
|---|---|---|---|---|---|---|---|---|---|---|---|---|---|
|  |  | Month 25 | Month 26 | Month 27 | Month 28 | Month 29 | Month 30 | Month 31 | Month 32 | Month 33 | Month 34 | Month 35 | Month 36 | |
| Screening trial: Primary care | | | | | | | | | | | | | | |
| Set up period + ethics | | | | | | | | | | | | | | |
| Recruitment surgeries | 5 | | | | | | | | | | | | | 60 |
| Cytopill clinics: first swallow | 250 | | | | | | | | | | | | | 2500 |
| Cytopill clinics: Repeat | 600 | | | | | | | | | | | | | 1200 |
| Sample processing and analysis | | | | | | | | | | | | | | |
| Endoscopy | 24 | | | | | | | | | | | | | 278 |
| Data analysis | | | | | | | | | | | | | | |
| Case-control study: Secondary care | | | | | | | | | | | | | | |
| Set up period + ethics | | | | | | | | | | | | | | |
| Cytopill: Barrett's cases first swallow | 100 | | | | | | | | | | | | | 500 |
| Cytopill: Barrett's cases follow up | 140 | | | | | | | | | | | | | 300 |
| Cytopill: dyspeptic controls | 100 | | | | | | | | | | | | | 500 |
| Sample processing and analysis | | | | | | | | | | | | | | |
| Data Analysis | | | | | | | | | | | | | | |

FIG. 9C

| Screening Trial: Primary Care | | | | | | | |
|---|---|---|---|---|---|---|---|
| CRF | | Demographics | GIS | ST12 | Impact of events | EQ-5D | STAI |
| | Baseline | X | X | X | | X | X |
| | Day 7 | | | X | X | X | X |
| | Day 90 | | | X | X | X | X |
| | | | | | | | |
| Specimens | | Cytosponge results | Endoscopy result | | | | |
| | Baseline | X | | | | | |
| | Within 40 Days | | X | | | | |
| Case-control study: Secondary care | | | | | | | |
| CRF | | Demographics | GIS | ST12 | Impact of events | EQ-5D | STAI |
| | Baseline | X | X | X | | X | X |
| | Day 7 | | | X | X | X | X |
| | Day 90 | | | X | X | X | X |
| | | | | | | | |
| Specimens | | Cytosponge results | Endoscopy results | | | | |
| | Baseline | X | X | | | | |

FIG. 10

BIOMARKER FOR BARRETT'S OESOPHAGUS

RELATED APPLICATIONS

This application is a continuation of U.S. Pat. No. 9,632,099, filed on Feb. 7, 2014, entitled, "Biomarker for Barrett's Oesophagus" which is continuation of U.S. Pat. No. 8,709,736, filed Jul. 9, 2010, entitled "Biomarker for Barrett's Oesophagus," which claims priority to GB 0920014.8, filed Nov. 13, 2009, each of which are incorporated by reference in their entirety for all purposes.

FIELD OF THE INVENTION

The present invention relates to the diagnostic methods and compositions for use in the same. More particularly, the invention related to the use of TFF3 in the diagnosis and detection of Barrett's Oesophagus using non-invasive, non-endoscopic methods.

BACKGROUND OF THE INVENTION

Oesophageal adenocarcinoma is increasing rapidly in western countries [1, 2] and patients usually present late with locally advanced disease leading to a dismal overall 5 year survival rate of 13% [3]. Barrett's oesophagus (BE), as defined by intestinal metaplasia, is the major identified risk factor for this cancer [4] and in those patients with oesophageal adenocarcinoma at presentation 90% have evidence of BE following shrinkage of the tumor post-chemotherapy [5]. However, because the majority (86%) of adenocarcinomas present de novo [6] (without prior diagnosis of BE) it is likely that a large number of BE patients remain undiagnosed in the population. This idea is supported by the high prevalence of BE (7-25% for segments of any length and 0.7-7% for long segment Barrett's) in asymptomatic patients who agreed to have a screening upper GI endoscopy when attending for colonoscopy in the US [7-9]. In keeping with these overall figures the prevalence of BE of any length was reported to be between 1 and 8% in all comers to endoscopy (reviewed in Pera, 2003 [10]). The only population prevalence data available suggests that BE is present in 1.6% of the general Swedish population [11].

Evidence from non-randomized retrospective studies demonstrated an improvement in 5-year actuarial survival from 13-43% to 62-100% in patients with surveillance-detected oesophageal adenocarcinomas [12-18]. These data suggest a potential benefit for early detection although lead time bias needs to be accounted for. Rapid advances in endoscopic technologies (reviewed by Reddymasu and Sharma [19]) as well as the development of chemoprevention strategies [20, 21] afford the opportunity to improve patients' outcomes if disease is detected early.

Thus, identification of undiagnosed BE patients should ultimately reduce mortality from oesophageal adenocarcinoma. To attain this objective, population-based screening for Barrett's is required. However there are major feasibility and cost implications for the wide-scale application of screening using the gold standard endoscopy [22].

Since the architecture of the tissue is well conserved, H&E slides may be reviewed by an expert gastrointestinal histopathologist but morphology alone is often not sufficient to diagnose BE and is open to subjectivity.

Novel screening strategies might include symptom nomograms, wireless capsule endoscopy and balloon cytology [23-25] but these have not yet been demonstrated to be sufficiently sensitive and specific for clinical use [26-28]. Recently, a study using a wireless video capsule attached to a string, allowed a more careful examination of the oesophagus and eliminated previous a major imaging drawback of fast oesophageal transit time with a reported sensitivity of 93.5% [29]. However, this approach does not permit a pathological diagnosis or the potential for implementing risk stratification using biomarkers.

Neither the British Society of Gastroenterology nor the American Gastroenterology Association currently recommend endoscopic screening for BE [22, 57] (recommendations grade C and B respectively, both based on cohort and case control studies). However, both professional organizations agree that surveillance is in order once BE is diagnosed. However, for surveillance to be of use, all Barrett's patients, symptomatic or asymptomatic would need to be diagnosed. This suggests population screening for BE may be recommended if a cost effective test could be developed. It is a problem that there is currently no suitable cost effective test available. The present invention seeks to overcome problem(s) in the art.

BRIEF SUMMARY OF THE INVENTION

The present invention relates to the use of TFF3 in the diagnosis and detection of Barrett's Oesophagus using non-invasive, non-endoscopic methods. In particular, the methods of the present invention relate to screening for Barrett's oesophagus (BE) in a subject comprising obtaining a sample of cells from the cellular surface of the oesophagus of a subject, determining the presence of Trefoil factor 3 (TFF3) in said sample of cells, wherein the presence of said TFF3 is indicative of said subject having BE. In particular embodiments, this non-invasive screening method employs cells taken from the subject wherein the cells are a mixed population of cells taken from the cellular surface of the oesophagus. More specifically, the oesophageal cells comprise cells from the oesophagus and gastric mucosa cells. It is a particular feature of the present invention that the method does not require the use of an endoscopy or other biopsy but is instead a non-invasive sampling method that simply uses the cells from an oesophageal brushing, preferably a non-endoscopic oesophageal brushing. Moreover, it is an advantage of the present invention that the screening method can be performed and yield positive results even in the absence of the subject having BE lesions.

In the methods described herein the cells are collected in a non-invasive manner using a swallowable device comprising an abrasive material capable of collecting cells from the surface of the oesophagus. For example, such a device comprises a capsule sponge that can be scraped along the oesophageal tract and withdrawn and the cells deposited thereon analysed for the presence of TFF3 protein or expression of TFF3. The methods described herein have a superior specificity and sensitivity as compared to the methods known in the art. For example, use of the TFF3 as a diagnostic marker for diagnosis of BE produces at least about high specificity of 80% and about 65% respectively. More particularly, the method has a specificity and sensitivity for diagnosis of BE of about 94% and about 78% respectively.

The methods of the invention may further be used to differentiate a mixed population of alimentary tract cells obtained from a subject suspected of having Barrett's oesophagus (BE) comprising determining the presence or expression of TFF3 on the surface of said cells, wherein the presence of TFF3 on the surface of any of the cells in the mixed population of cells identifies said cells as being from a BE lesion in the alimentary tract.

The TFF3 may be detected using any method known in the art. Advantageously, the presence of TFF3 is detected in an immunoassay using an antibody specific for TFF3. In other embodiments, the TFF3 is detected on the surface of the cells using an immunohistochemical detection method. The diagnosis of BE may be further confirmed by staining the cells with an Alcian Blue stain which is known to stain positive for cells taken from BE lesions.

BRIEF DESCRIPTION OF SEVERAL VIEWS OF THE DRAWINGS

FIG. 9A-9C shows a timeline.

FIG. 10 shows a summary chart.

DETAILED DESCRIPTION OF THE INVENTION

Figure 1:
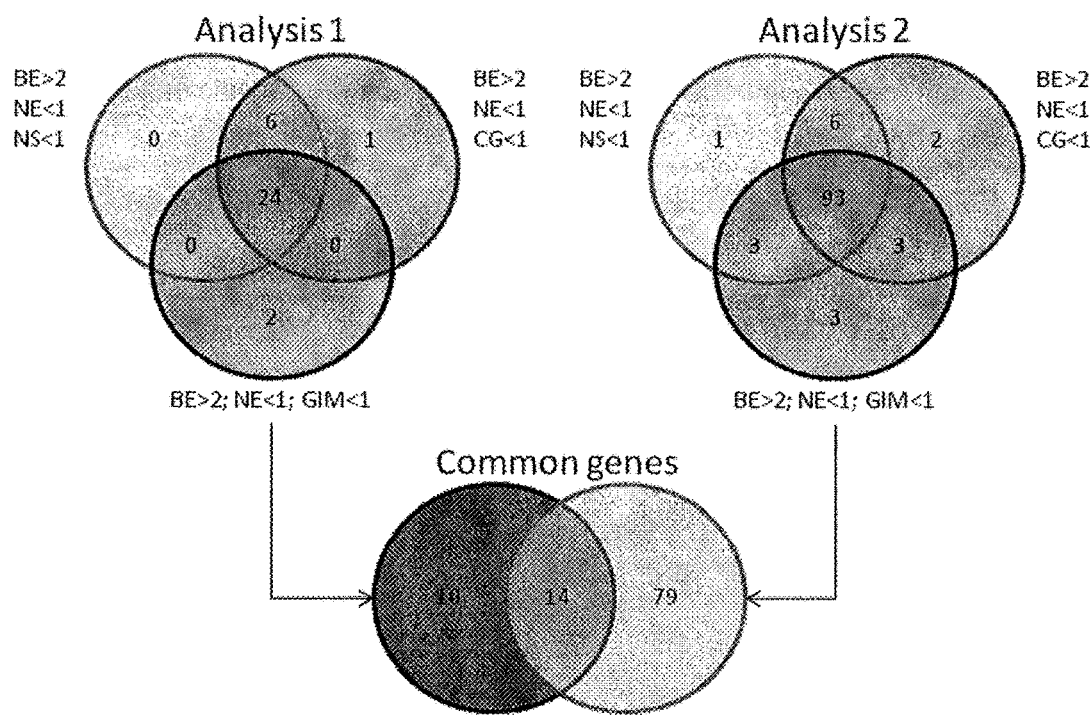
FIG. 1: Venn diagram of the number genes identified by analyses 1, 2 and genes common to the two microarray analyses. Analysis 1 and 2 yielded 24 and 93 putative targets respectively. A total of 14 genes common to both analyses were validated further. (BE: Barrett's oesophagus, NE: normal oesophagus, NS: normal stomach, CG: chronic gastritis, GIM: gastric intestinal metaplasia).

We disclose TFF3 as a biomarker for BE. We have demonstrated for the first time that microarray analysis can be directly applied to the clinic in the context of BE. TFF3 was identified as one of a number of candidate markers by selection from a large volume of publically available DNA microarray data. The inventors demonstrated that it was over-expressed in BE compared to adjacent normal tissues at the RNA and protein level. We disclose its use in a novel minimally invasive, non-endoscopic screening strategy.

The invention provides improved diagnostic accuracy via identification and validation of biomarker(s) that have the ability to clearly distinguish between cells from BE, normal gastric and squamous oesophageal cells since the preferred capsule-sponge mode of collection samples cells from the stomach to the oro-pharynx. The biomarker provided is highly specific which has the advantage of minimising cost since in a screening programme, patients with a positive capsule test would need to undergo endoscopy to verify the diagnosis and allow for multiple biopsies to be performed to exclude dysplasia.

Trefoil factors are mucin-associated petides thought to be involved in multiple biological functions including repair of the mucosa through enhancement of restitution (mucosal repair by cell migration) and modulation of stem cells differentiation as well as interaction with mucins and modulation of the mucosal immune response [40-43]. In the gastrointestinal tract, TFF1 and 2 are mainly expressed by the gastric epithelium [42] while TFF3 is expressed by the intestine and intestinal metaplasia of the stomach and oesophagus [44, 45]. TFF3 expression has been demonstrated to be increased by gastro-oesophageal reflux disease [45], and transient overexpression of the homeodomain protein CDX2 [46], linking its expression to the development of BE. Interestingly, there have been a number of publications concerning the development of novel cytological methods using TFF3 to detect thyroid follicular carcinomas [47, 48] and it has been suggested that TFF3 could also be detected in the serum of patients with high-grade endometrial carcinomas [49]. It might therefore be possible to develop a serum based assay to screen for BE using TFF3 as a marker.

Dopadecarboxylase metabolizes 3,4-dihydroxyphenylalanine (DOPA) to dopamine and 5-hydroxytryptophan to serotonin [50]. Overexpression of DDC is also a feature of a number of malignancies ranging from retinoblastomas [51, 52] to small cell lung cancers [53], prostate cancers [54] and gastric cancers with peritoneal disseminations [55]. In most of these tumor types, an effort has been made to use DDC diagnostically using PCR techniques in biopsies [54, 56] or cytological specimens [55]. DDC may therefore be of interest as a biomarker for malignant conversion in Barrett's and due to the poor immunohistochemistry staining a PCR based assay may be more applicable.

An advantage of this novel capsule sponge test is that it can be performed in primary care. Since the TFF3 analysis presented here relies on standard immunohistochemical techniques it is an objective test that would be readily applicable to clinical pathology laboratories in a cost effective manner. Furthermore, in the future other assays could be applied to these sponge samples such as PCR based assays to determine gene expression levels of multiple biomarkers or DNA based assays to determine methylation status or loss of heterozygosity. Such methodologies might increase the price of the test but may also be informative with regards to the risk of progression to cancer. The typical circumscribed appearance of TFF3 positivity and the strength of the staining make it particularly suited for automation thus potentially further reducing the cost of a screening program incorporating this methodology.

For such a BE screening test, it is advantageous to have a high specificity to avoid calling patients for unnecessary endoscopies with the inherent generation of anxiety, high costs and risks of an invasive procedure that this would entail. With TFF3 we obtained a very high specificity of 94% and an adequate sensitivity of 78%. It is unlikely for a single marker to provide both a high sensitivity and specificity. It is reasonable to accept that a device like the capsule sponge, while sampling from the entire surface of the mucosa, will only collect cells that detached. Small foci of IM, yielding TFF3 positivity, may be missed, explaining the sensitivity of 78%.

TFF3

In the search for a robust marker, the inventors undertook an intensive genetic and biochemical analysis. Initially, the inventors analysed data relating to approximately 54,000 genes. This initial screening effort was based on a combination of various available data sets. The aim was to identify candidate markers which might be increased in Barrett's oesophagus but would not show an increase in non-Barrett's tissue such as gastric cardia or squamous oesophagus. This was an impartial analysis with no bias or choice introduced in selection of candidates. In other words, this could be regarded as a genome wide search. Promising candidates were taken forward for validation.

An initial validation step was based on PCR amplification. Candidates passing this test were taken forward.

A further step towards validation was to obtain antibodies recognising the candidates. Those candidates which could be recognised by antibodies were taken forward for further validation.

A further validation step was undertaken by tissue staining. Those antibodies capable of showing a differentiation/discrimination were taken forward for further validation.

Antibody staining was then validated on samples of cells which were obtained non-specifically (for example by use of a capsule sponge sampling technique).

The culmination of the design and application of each of the rigorous screening steps devised and implemented by the inventors was the identification of TFF3 as a robust marker for Barrett's oesophagus.

The initial genetic screening approach supplied 14 candidates. The various validation steps narrowed these 14 candidates down to only 2 candidates. One of these showed only deep tissue staining together with infrequent or rare staining patterns and behaved as a very poor marker. The conclusion of the screening and multiple validation steps was that TFF3 was the only consistent and robust marker for use in detection of Barrett's oesophagus in this setting.

TFF3 showed an initial sensitivity of 79% and an initial specificity of 94%. These findings are demonstrated in the examples section.

Furthermore, although not powered to determine accuracy of the test as a primary outcome measure, when non-specific sampling techniques such as the cytosponge sampling technique were used, TFF3 demonstrated a sensitivity of 90% and a specificity of 94% for detection of Barrett's oesophagus.

It is an advantage of the invention that these levels of sensitivity and specificity are so high. Moreover, it was an unexpected finding of the inventors at such high levels of specificity would be associated with TFF3.

Suitably sensitivity is 79% or more. Suitably sensitivity is 90% or more.

Suitably specificity is 94% or more.

Sample

Suitably the sample comprises cells from the subject of interest. Suitably the sample comprises oesophagal cells from the subject of interest. Suitably the sample is non-endoscopic ie. suitably the sample is obtained without the use of an endoscope. Endoscopic sampling is an invasive technique. Furthermore, endoscopic sampling is a targeted technique where biopsies are taken at intervals along the oesophagus, or where lesions are visually identified by the operator and specifically targeted for biopsy. Suitably the invention does not involve endoscopic samples such as endoscopic biopsies.

Prior art techniques for detecting Barrett's oesophagus have typically involved a targeted sample such as an endoscopic biopsy together with a proliferation marker such as MCM2. This essentially asks the question whether, in a specifically chosen sample obtained by a skilled endoscopic operator, there are any cells which are proliferating (e.g. dys-regulated). Although this is clearly useful, it is not suitable for population screening due to the expensive, time consuming and invasive nature of the targeted endoscopic sampling.

A key principle of the invention is to provide a marker which is specific for Barrett's oesophagus. The marker is specific for Barrett's oesophagus in the sense of not naturally occurring in unrelated tissues such as normal squamous oesophagus, or gastric cardia (stomach). Thus, by providing a marker with these specific characteristics, the invention advantageously provides a marker targeted to detection of Barrett's oesophagus cells. In this way, the invention advantageously avoids the need for targeted sample collection. Thus, the invention advantageously involves samples obtained by non-targeted sample collection such as sampling the entire surface of the oesophagus rather than only targeting areas of suspected lesions (Barrett's).

Thus, suitably sample does not comprise an endoscopic biopsy.

Suitably the sample may comprise oesophical brushings or surface cells. Oesophagal brushings may be obtained using an endoscope or by other means; suitably when the sample comprises oesophagal brushings they are obtained by non-endoscopic means.

Suitably the sample may comprise cells sampled from the entire oesophagal lumen.

Suitably the sample may comprise both oesophagal and non-oesophagal cells.

Suitably the sample may comprise oesophagal cells together with gastric cardia cells.

Most suitably, the sample may comprise cells collected using a capsule sponge type sampling technique.

Especially suitable sampling techniques are described in the examples section.

Examples of suitable samples include oesophagal brushings (whether endoscopically or non-endoscopically obtained), samples obtained via balloon cytology, samples obtained via capsule sponge sampling. Most suitably, a sample comprises cells obtained via capsule sponge sampling. It can therefore be appreciated that TFF3 possesses certain properties which make it advantageous as a biomarker for Barrett's oesophagus.

Firstly, TFF3 exhibits luminal surface expression. This means that the sample to be analysed need only be collected from the surface of the oesophagal lumen. This advantageously avoids the need for a biopsy such as an endoscopic biopsy. Moreover, this advantageously avoids the need to preserve tissue architecture in the sample being analysed.

A further advantage of TFF3 is that it is able to differentiate between the oesophagal lumen and the gastric mucosa. Specifically, TFF3 is not expressed in the gastric mucosa (e.g. gastric cardia/stomach). This has a specific advantage that if cells of the gastric mucosa are included in the sample, then TFF3 is still able to function as a robust biomarker for Barrett's. This is because TFF3 is not expressed in gastric mucosa cells, and therefore no false positives occur even when the sample comprises cells of the gastric mucosa. Thus, this capacity for differentiation is another robust advantage of TFF3 in the present invention. This property is in particularly sharp contrast to other members of the TFF3 family of proteins since TFF3 appears to be unique amongst TFF proteins in not identifying cells of the gastric mucosa.

Thus it can be appreciated that the choice of TFF3 by the inventors provides a degree of specificity which has not yet been provided in any prior art approach to screening for Barrett's oesophagus. The present inventors were the first to actively seek, and to successfully provide, a marker capable of such focused discrimination. Moreover, sampling techniques in the prior art have been confined to oesophagus. Thus, the inventors are the first to have identified the utility of a marker having the properties disclosed herein, as well as being the only ones to have identified such a marker.

A non-endoscopic capsule sponge device which has been approved by the Medical Health Regulatory Agency (Ref n# CI/2007/0053) in the UK may be used for sample collection. A pilot study demonstrated that this device is acceptable to patients and could be used in primary care [30], [31]. The device consists of a polyurethane sponge, contained within a gelatin capsule, which is attached to a string. The capsule is swallowed and dissolves within the stomach after 3-5 minutes. The sponge can then be retrieved by pulling on the string. Initial studies were performed using a cell monolayer stained with a proliferation marker mcm2. This gave a suboptimal sensitivity and specificity of 67.5% and 67.4% respectively and sample heterogeneity meant that the whole sample had to be processed and analyzed for this single biomarker. More recently, we have processed the cytological specimen to a pellet which can then be embedded in paraffin thus preserving the tissue architecture. This can then undergo histological assessment and in addition, multiple immunohistochemical markers may be used on a single sample [31]. Thus, mode of sample collection is particularly suitable for use in the present invention.

Mode of Detection

The marker may be detected by any suitable means known in the art. For example, the marker may be detected using nucleic acid based techniques such as RNA analysis.

Suitably, the marker is detected at the protein level.

Most suitably, the marker is detected using antibodies such as anti-TFF3 antibodies.

It is an advantage of the invention that quantitative levels of expression need not be determined. It is an advantage of the invention that mere presence/absence of the marker is sufficient to aid the diagnosis of Barrett's oesophagus.

Thus it is an advantage of the invention that a qualitative measurement (e.g. simple presence or absence) is sufficient to aid the diagnosis without needing to resort to quantitative measurement.

It is an advantage of the invention that controls or reference samples are not necessary, since it is possible to work the invention scoring only a simple presence or absence of TFF3.

It is an advantage of the invention that TFF3 may be analysed on its own. In other words, combinations with other markers are not necessary for performance of the invention.

The methodology used for marker identification ensured high specificity since we identified the best discriminators between BE and NE and GM but not necessarily sensitivity because the sample size of the microarrays was not high enough. Current screening programs for prostate (prostate serum antigen), cervical (Papanicolaou test) and colon cancer (fecal occult blood test (FOBT)) have accepted sensitivities of 30-96% respectively and specificities of 77-100% respectively [59-61]. The positive predictive value of PSA for prostate cancer and of FOBT for colon cancer is 47% and 2.2-17.7% respectively [59, 60]. It may therefore be desirable to identify additional markers that, used in conjunction of TFF3, would offer a high sensitivity without loss of specificity. Naturally, if the skilled worker wishes to analyse markers other than TFF3 in parallel, then this does not adversely effect the invention. For example, it may be desired to use Alcian Blue staining in parallel with TFF3 analysis. Alcian blue stains goblet cells and typically stains the same cells as express TFF3. Alcian blue may be used to confirm Barrett's oesophagus in biopsies. Thus, in one embodiment, the invention relates to analysing a sample for the expression of TFF3, and analysing said sample using Alcian blue staining.

The invention provides non-endoscopic screening biomarkers for Barrett's oesophagus. These find application in microarray analysis and in the clinic. In particular the invention finds application in population screening such as non-invasive screening for Barrett's.

Barrett's oesophagus (BE) predisposes to oesophageal adenocarcinoma but the majority of patients are undiagnosed. A non-endoscopic cytological screening device, called a capsule sponge, makes population-based screening for BE a feasible option. However, due to the mixed cell population retrieved by the capsule sponge, biomarkers specific for BE are required. The present invention provides the TFF3 biomarker which is specific for BE, in particular specific for BE amongst the heterogeneous cells in samples such as those collected by capsule sponge sampling. In other words, TFF3 is an excellent marker for BE screening since it is expressed at the luminal surface of BE but not in adjacent tissue types and may be applied to a non-endoscopic screening device.

Further Applications

The invention may relate to use of TFF3 as a BE biomarker when used in combination with non-endoscopic sampling.

TFF3 has the advantage of luminal surface expression and differential expression with the gastric mucosa.

The invention may relate to use of TFF3 as biomarker for BE where sensitivity and specificity are at least 79% and 94% respectively. The inventors were surprised by the unexpectedly high levels of specificity and sensitivity shown for TFF3.

The present invention provides methods of aiding the diagnosis of Barrett's oesophagus or Barrett's associated dysplasia in a subject, said method comprising sampling the cellular surface of the oesophagus of said subject, and assaying the cells for the presence of TFF3, wherein detection of TFF3 indicates increased likelihood of the presence of Barrett's or Barrett's associated dysplasia. In particular, the sampling is efficient because it is not directed to a particular site within the oesophagus but instead the sample of cells is taken across the entire surface of the oesophagus. This has the advantage of avoiding more invasive sampling techniques such as biopsy collection techniques which penetrate below the surface of the oesophagus.

In addition to the detection of TFF3, the cells may also be monitored to determine the presence of other markers of BE such as those markers that are indicative of brush border proteins such as villin or moesin, mucin genes, brush border enzymes such as alkaline phosphatase, homeobox genes such as Cdx1 and/or Cdx2, cytokeratins such as CK8/18 for columnar cells, or any marker known to be differentially expressed in Barrett's versus normal oesophageal surface cells.

Preferably in addition to TFF3, the additional marker may be selected from the group consisting of proliferation markers such as Ki67 and Mcm proteins, proliferation and DNA damage markers such as PCNA, cyclins such as cyclin D and/or cyclin A, abnormal p53, loss of p16, aneuploidy or any marker known to correlate with the degree of dysplasia. More preferably the marker is Mcm2 or Cyclin A.

In the methods the invention the sampling of the cellular surface of the oesophagus comprises the steps of
(i) introducing a swallowable device comprising abrasive material capable of collecting cells from the surface of the oesophagus into the subject, (ii) retrieving said device by withdrawal through the oesophagus, and (iii) collecting the cells from the device.

Preferably step (i) comprises introducing a swallowable device comprising abrasive material capable of collecting cells from the surface of the oesophagus into the subject's stomach.

In another aspect, the invention provides a method as described above further comprising analysing the chromosomal composition of the cells, wherein detection of abnormal karyotype indicates an increased likelihood of dysplasia.

In another aspect, the invention provides a kit comprising a swallowable device comprising abrasive material capable of collecting cells from the surface of the oesophagus, together with printed instructions for its use in detection of TFF3 to diagnose Barrett's oesophagus or Barrett's associated dysplasia.

In another aspect, the invention provides a kit as described above further comprising a local anaesthetic. Preferably said local anaesthetic is a spray or lozenge, preferably a spray.

In another aspect, the invention provides a kit as described above further comprising a container for receiving said swallowable device after withdrawal, said container having a quantity of preservative fluid therein. Preferably the container is a watertight container. Preferably the preservative fluid is a cell preparation fluid. Preferably said fluid is thin preparation fluid for production of slides for examination of the sampled cells.

In another aspect, the invention provides a kit as described above wherein said device comprises a capsule sponge.

In another aspect, the invention provides a kit as described above wherein said swallowable device comprises withdrawal means such as string.

In another aspect, the invention provides a kit as described above further comprising a device for severing said withdrawal means. Preferably said device comprises a blade or scissors.

In the kit there also may be a container for administering drinkable fluid, such as water, to the subject. The kit may also contain a local anaesthetic spray or lozenge to facilitate the deliver and sampling of the oesophagus cells using the sponge device.

In another aspect, the kit invention provides a kit as described above further comprising reagents for use in the detection of at least one marker selected from the group consisting of brush border proteins such as villin or moesin, mucin genes, brush border enzymes such as alkaline phosphatase, homeobox genes such as Cdx1 and/or Cdx2, cytokeratins such as CK8/18 for columnar cells, or any marker known to be differentially expressed in Barrett's versus normal oesophageal surface cells.

Barrett's Oesophagus can occur without dysplasia. Approximately 1% of patients with Barrett's oesophagus will develop dysplasia each year. At any given time, approximately 20% of patients with Barrett's oesophagus will have dysplasia. Cancer such as adenocarcinoma develops from dysplasia and is regarded as one extreme form of dysplasia, even though pathologically the conditions clearly differ. It is desirable to obtain an early diagnosis of adenocarcinoma and the present invention is concerned with such detection and diagnosis of a single progressive disease state that has recognisable discrete stages. These stages comprise Barrett's oesophagus, Barrett's oesophagus associated dysplasia including adenocarcinoma, which arises therefrom.

In these diagnostic methods, the cells are sampled from the surface of the oesophagus using a swallowable abrasive material, which material is retrieved from the patient and from which the cells are subsequently separated for analysis to determine the presence of TFF3. Preferably substantially the entire surface of the oesophagus is sampled, preferably the entire surface. In the present invention, there is no need to focus only on Barretts oesophagus lesions as the inventors have found that the presence of TFF3 is associated only with BE and as such TFF3 can be used to specifically diagnose whether a mixed population of cells obtained from the entire surface of the oesophagus have therein cells that are from BE lesions.

By abrasive is meant that the material is capable of removing cells from the internal surface of the oesophagus. Clearly, since this is meant for use in a subject's oesophagus, 'abrasive' must be interpreted in the light of the application. In the context of the present invention the term 'abrasive' has the meaning given above, which can be tested by passing the material through the oesophagus in an appropriate amount/configuration and examining it to determine whether cells have been removed from the oesophagus.

The material used in the collection device must be sufficiently abrasive to sample any dysplastic cells present in the oesophagus. Preferably the material is sufficiently abrasive to sample any Barrett's or adenocarcinoma cells present. In a most preferred embodiment, preferably the material is sufficiently abrasive to be capable of sampling the whole oesophagus ie. so that some squamous cells are collected together with any Barrett's and/or columnar and/or adenocarcinoma cells which may be present. This is advantageous because squamous cells are more difficult to remove than dysplastic cells and so their sampling provides a control to the operator such that if normal squamous cells are removed by the material then the chances of having not sampled the cells of interest such as Barrett's or dysplastic cells (if present), which are easier to remove than normal squamous cells, is correspondingly small.

Preferably the swallowable abrasive material is expandable. In this embodiment, preferably the abrasive material is of a smaller size when swallowed than when withdrawn. An expandable material may be simply a resilient material compressed such that when released from compression it will expand again back to a size approximating its uncompressed size. Alternatively it may be a material which expands e.g. upon taking up aqueous fluid to a final size exceeding its original size.

In other words, preferably the material of the device expands, swells, inflates or otherwise increases in size between swallowing and withdrawal. Preferably the device is auto-expandable ie. does not require further intervention between swallowing and expansion. Preferably the device is not inflatable. Preferably the device expands by unfolding, unfurling, uncoiling or otherwise growing in size following removal of restraint after swallowing. Preferably the material of the device is compressible and reverts a size approximating its uncompressed size following swallowing. Preferably the device is constructed from a compressed material which is releasably restrained in a compressed state. Preferably the material is released from restraint after swallowing, allowing expansion of the device/material before withdrawal.

Preferably the device comprises compressible material which is compressed into capsule form. Preferably the compressible material is in the form of sponge material.

Preferably the compressed sponge is at least partially surrounded by a soluble and/or digestible coat such as a capsule coat. Preferably the sponge is indigestible. Preferably the capsule coat is at least partially formed from gelatin. Preferably the capsule coat is fully formed from gelatin.

In one embodiment it may be desirable to make the whole device out of digestible material to increase safety in case of a device becoming lost in the subject. Naturally the abrasive material would need to be digested at a slower rate than the capsule and the cord would need to be similarly slowly digested. Preferably the abrasive material is non-digestible. Preferably the cord is non-digestible.

Preferably the abrasive material comprises polyurethane, preferably polyurethane sponge.

Preferably the device is a capsule sponge. As will be apparent from the specification, a capsule sponge is a device comprising compressible sponge as the abrasive material, which sponge is compressed into a capsule shape, which capsule shaped compressed sponge is preferably reversibly restrained in its compressed state by at least a partial coat of soluble and/or digestible material such as gelatine. Preferably the device is a capsule sponge as supplied by Francois Venter at Medical Research Council, South Africa. Preferably the device is a capsule sponge as manufactured by Medical Wire and Equipment (MWE), Corsham, Wiltshire, UK.

Preferably the sample does not comprise endoscopically collected material. Preferably the sample does not comprise endoscopic biopsy. Preferably the sample does not comprise endoscopic brushings.

It is a feature of the invention that the sampling is not directed e.g. visually directed to any particular part of the oesophagus but rather the sponge is scraped along the entire surface of the oesophagus and obtains a heterogeneous sample of cells from the tract. It is a further advantage of the invention that a greater proportion of the surface of the oesophagus is sampled than is achieved by prior art techniques such as endoscopic biopsy (which samples approximately 1% of the surface) or endoscopic brushing. Preferably at least 10% of the oesophageal surface is sampled, preferably at least 20%, preferably at least 30%, preferably at least 40%, preferably at least 50%, preferably at least 60%, preferably at least 70%, preferably at least 80%, preferably at least 90%. In a most preferred embodiment, preferably substantially the entire oesophagus is sampled, preferably the whole inner lumen of the oesophagus is sampled. This applies equally to the in vitro sample even when the method of the invention does not include collection of the sample.

The invention will now be described by way of examples, which are intended to be illustrative and are not intended to limit the scope of the appended claims. Reference is made to the following figures.

Certain Abbreviations are used, including BE Barrett's oesophagus, CG Chronic gastritis, GC Gastric cardia, GIM Gastric intestinal metaplasia, GM Gastric mucosa, IM Intestinal metaplasia, NE Normal oesophagus, NS Normal stomach.

EXAMPLES

Overview

We hypothesized that biomarkers for BE can be identified by combining and re-analyzing a number of previously published upper gastrointestinal microarray datasets. In this way we identify putative biomarkers from a combinatorial in silico analysis and then perform validation studies on independent samples at the RNA and protein level before finally applying any candidates to samples from a capsule sponge collected from an independent cohort of Barrett's patients and healthy controls.

Three publically available microarray datasets were used to identify putative biomarkers present in BE but absent from squamous oesophagus (NE) and gastric mucosa (GM). Validation was performed by QPCR (n=10 each of NE, BE, GM) and immunohistochemistry (NE n=20, BE n=21, GM n=24, duodenum n=18).

2/14 genes identified, dopa-decarboxylase (DDC) and Trefoil Factor 3 (TFF3), were confirmed by QPCR to be upregulated in BE compared to NE ($p<0.01$) and GM ($p<0.01$ and $p<0.05$ respectively). Immunohistochemistry confirmed that DDC protein expression was restricted to BE but was confined to <1% of the cells within the crypt compartment. TFF3 protein was expressed to high levels at the luminal surface of BE compared to absent expression in NE and GM ($p<0.001$).

The biomarker was then prospectively evaluated on capsule sponge specimens from 47 BE patients and 99 healthy controls. Using the capsule sponge 36/46 BE patients (1 inadequate sample) and 6/96 controls were positive for TFF3 giving a sensitivity of 78% and a specificity of 94%.

Example 1: Identification of Putative Targets

We used a strategy involving three microarray datasets to screen for candidate genes that were specifically expressed in BE. Twenty four genes from analysis 1 (Hao/Boussioutas) were found to be statistically overexpressed in BE ($\log_2$ ratio>2) compared to NE ($\log_2$ ratio<1) and GM ($\log_2<1$). Using the same $\log_2$ ratio comparisons 93 genes were identified from analysis 2 (Greenawalt/Boussioutas), (FIG. 1).

Microarray Analysis

The invention is based in part on a substantial leap forward in the translation of high throughput laboratory results into an assay that can be used in the clinic. The microarray experiments were not designed specifically to identify markers distinguishing between BE, NE and GM and to our knowledge no dataset including normal oesophagus, Barrett's oesophagus and normal gastric mucosa exists. Furthermore, the microarray platform by of Hao et al. [32] was different from the platform used by Boussioutas et al. [33] and Greenawalt et al. [34]. This explains the lower number of candidates identified in the first (Hao-Greenawalt; n=33) compared with the second analysis (Boussioutas-Greenawalt; n=111) (see below). However, very stringent statistical criteria were set to reduce the effect of these shortfalls which also reduced the number of putative targets.

A search of the literature (PubMed) and public gene expression microarray databases (GEO, Stanford Microarray Database) was performed to identify microarray datasets pertaining to gene expression patterns in IM-containing BE, NE (normal squamous oesophagus) and gastric mucosa (normal stomach (NS), chronic gastritis (CG) and gastric IM (GIM)). These tissues were selected since they will sampled by the capsule sponge.

CG and GIM were chosen to represent upper GI inflammation and *Helicobacter*-induced IM respectively, which may be present in the screened population and need to be distinguished from BE. Three datasets, detailed in Table 1, were selected for analysis based on the following criteria: a) data was generated from more than 5 samples per relevant tissue type and; b) the arrays used contained >10000 cDNA or oligonucleotide probes. All three microarray studies involved the hybridisation of differentially labelled test and reference cDNA to a spotted cDNA array, and data from all three studies were available in the form of normalised test:reference hybridisation signal intensity ratios. Different analyses were performed to generate a single gene list (FIG. 1). Analysis 1: Hao et al. [32] (15 NE and 14 BE) was analyzed, using a parametric test (Welch t-test) with Bonferroni correction, to identify genes which were differentially expressed between the two groups and whose expression was significantly upregulated in BE ($log_2$ ratio>2) compared to NE, (p<0.0001). This list was then used to interrogate Boussioutas et al. [33] (57 gastric mucosa samples (GM) comprising NS, CG and GIM) for genes that were under-expressed in GM (<1). Analysis 2: Greenawalt et al. [34] (39 NE and 26 BE) was analyzed in a similar fashion to dataset 1 to produce a set of genes with $log_2$ ratios BE>2, NE<1 and GM<1 (from Boussioutas et al. [33]). Data analysis was done using GeneSpring GX version 7.3 (Agilent, Palo Alto, Calif., USA). Genes common to both analyses were selected and ranked in order of statistical significance and enrichment in BE for subsequent validation.

TABLE 1 microarray datasets selected for analysis

| | Specimens | Array | Reference | Normalisation | Source of data |
|---|---|---|---|---|---|
| Hao [32] | 15 Normal oesophagus 14 Barrett's oesophagus | Spotted cDNA array (42,000 spots) | Commercial human RNA | Intensity-dependent | Stanford microarray database (http://genome-www5.stanford.edu) |
| Boussioutas [33] | 8 Normal stomach 27 Chronic gastritis 22 Gastric IM | Spotted cDNA array (11,500 spots) | Pool of 11 normal gastric specimen | LOWESS normalisation | GEO Accession GSE2669 |
| Greenawalt [34] | 39 Normal oesophagus 26 Barrett's oesophagus | Spotted cDNA array (11,500 spots) | Pool of 11 cell lines | LOWESS normalisation | ArrayExpress ID E-MEXP-692 |

It was found that 14 genes (table 3 and FIG. 1) were common to both analyses.

TABLE 3

Putative biomarkers, primer sequences and PCR conditions

| Name | Symbol | Accession n# | Forward primer | Reverse primer | Annealing T° C. |
|---|---|---|---|---|---|
| Anterior gradient 2 | AGR2 | NM_006408 | TTGTCCTCCTCAATC TGGTTTATG (SEQ ID NO. 1) | GCAGGTTCGTAAGCA TAGAGAC (SEQ ID NO. 2) | 53 |
| ATPase, Cu2+ transporting, polypeptide | ATP7B | NM_000053.2 | ACAAAGCACTAACCC AAAGAGAC (SEQ ID NO. 3) | ATATTCAAGACGCAA GACTTACAATG (SEQ ID NO. 4) | 53 |
| Death-associated protein kinase-1 | DAPK1 | NM_004938 | AACTACGAATTTGAG GATGAATACTTC (SEQ ID NO. 5) | GATCCAGGGATGCTG CAAAC (SEQ ID NO. 6) | 53 |
| M-Dopa decarboxylase | DDC | NM_000790 | CTTCGCCTACTTCCC CACTG (SEQ ID NO. 7) | CTTTGGTAGTTCCAG CATCTTCC (SEQ ID NO. 8) | 55 |
| Fructose-1,6-biphosphate decarboxylase | FBP1 | NM_000507 | CACTGAGTACATCCA GAGGAAG (SEQ ID NO. 9) | CTTCTTGTTAGCGGG GTACAG (SEQ ID NO. 10) | 57 |
| Flavin containing monooxygenase | FMO5 | NM_001461.1 | GGACAGGCGACACTA ACAGG (SEQ ID NO. 11) | CCTTTCAAAGCAGAC AGGTTCC (SEQ ID NO. 12) | 53 |

TABLE 3-continued

Putative biomarkers, primer sequences and PCR conditions

| Name | Symbol | Accession n# | Forward primer | Reverse primer | Annealing T° C. |
|---|---|---|---|---|---|
| Forkhead box A3 | FOXA3 | NM_004497.2 | TGCTGCCTCGACCACCAC (SEQ ID NO. 13) | AGTGAAATAGGGTGTGGAGGAAG (SEQ ID NO. 14) | 56 |
| Fucosyl-transferase 4 | FUT4 | NM_002033.2 | N/A* | N/A* | N/A |
| golgi phosphoprotein 2 | GOLPH2 | NM_177937.1 | AGTGTGAGGAGCGAATAGAAGAG (SEQ ID NO. 15) | TGTCTGGGACTTGCTGTTACC (SEQ ID NO. 16) | 53 |
| lysozyme (renal amyloidosis) | LYZ | NM_000239.1 | GACCTAGCAGTCAACATGAAGG (SEQ ID NO. 17) | CCATTCCCAATCTTTTCAGAGTTC (SEQ ID No. 18) | 53 |
| phospholipase C-like 2 | PLCL2 | NM_015184.2 | CCATCAAGGAAGTGAGAACAGG (SEQ ID NO. 19) | ATATATGACGGAAAACGCACAATC (SEQ ID NO. 20) | 56 |
| ribonuclease, RNase A family, 4 | RNAse4 | NM_194430 | GCAGAGGACCCATTCATTGC (SEQ ID NO. 21) | CGCAGGAATCGCTGGTAC (SEQ ID NO. 22) | 57 |
| Trefoil factor 1 | TFF1 | NM_003225 | CCCCGTGAAAGACAGAATTGTG (SEQ ID NO. 23) | CGTCGATGGTATTAGGATAGAAGC (SEQ ID NO. 24) | 53 |
| Trefoil factor 3 | TFF3 | NM_003226.2 | TCTGGGAGCTTGACAAAGGC (SEQ ID NO. 25) | GGATTGTTTGCTTGGGGAAGG (SEQ ID NO. 26) | 56 |

*N/A: qPCR analysis was not performed since no suitable positive control could be identified It is interesting to note that only 2 out of 14 targets were validated by qPCR and in most cases this was because the expression level of the putative markers was similar in GM (cardia) and BE. This suggests that the expression profile of the cardia is closer to BE than normal gastric mucosa, chronic gastritis and intestinal metaplasia of the cardia. It has previously been demonstrated that the kinome [38] and the expression profile [39] of BE have strong similarities to that of gastric cardia.

Example 2: Validation of Targets

Human Specimens

Patients undergoing upper GI endoscopy were recruited to this biomarker study from Addenbrooke's Hospital following approval by the Local Research Ethics Committee. All patients with BE, had an endoscopically visible columnar lined segment of more than 3 cm and a histopathological diagnosis of specialized intestinal metaplasia. For NE samples were taken 2 cm above the z-line in patients with BE and 2 cm above the gastro-oesophageal junction (GOJ) in patients without BE who were undergoing symptomatic evaluation as part of the routine surveillance service.

The microarray targets were validated using real-time PCR (RT-PCR) in 10 samples from each of BE, NE (5 from Barrett's patients and 5 from non-Barrett's patients with a normal oesophagus) and 10 GM samples (collected from the cardia of Barrett's patients, table 2). The cardia was defined as 1 cm below the upper border of the gastric folds at the lower oesophagus in non-Barrett's patients. A frozen section from each snap frozen Barrett's specimen was analyzed by a histopathologist to confirm the presence of IM prior to RNA extraction.

The protein expression of putative biomarkers validated by RT-PCR was confirmed by immunohistochemistry on paraffin embedded section from an independent cohort of 21 non-dysplastic BE, 20 NE, 24 GM and 18 non-inflamed duodenum specimens which were used as a control columnar-lined tissue containing goblet cells (table 2).

TABLE 2

Clinical characteristics of cohorts

| | Number of patients | Age (median [95% CI]) | M:F ratio | Length BE (cm [95% CI]) |
|---|---|---|---|---|
| Real time PCR | | | | |
| Normal oesophagus | 10 | 62 [56-59] | 1.5:1 | 8.3 [6-10]* |
| Barrett's oesophagus | 10 | 65 [61-68] | 2:1 | |
| Gastric mucosa | 10 | 63 [56-69] | 1.5:1 | |
| Immunohistochemistry | | | | |
| Normal oesophagus | 20 | 59 [49-71] | 0.8:1 | 4.3 [3.2-5.3] |
| Barrett's oesophagus | 21 | 70 [63-78] | 2:1 | |
| Gastric mucosa | 24 | 62 [57-66] | 1.5:1 | |
| Duodenum | 18 | 58 [24-75] | 1:1 | |
| Capsule sponge | | | | |
| Control patients | 99 | 60 [58-62] | 1:1 | 6.5 [4.9-7.4] |
| Known Barrett's | 47 | 64 [60-67] | 3:1 | |

*indicate that the length of the BE samples used for RT-PCR is statistically longer than those for immunohistochemistry ($p < 0.01$)

RNA Extraction Real-Time PCR

Total RNA from biopsies was extracted by using Trizol (Invitrogen). 1 μg of RNA was reverse transcribed using SuperScript II reverse transcriptase kit (Invitrogen, Paisley, UK) in 20 μL of total reaction solution. The primers used are listed in Table 2. Positive controls were identified for each primer pair using a screen of 25 cells lines from different tissue origins. Quantitative PCR was performed on 2 μL of cDNA with the SYBR Green JumpStart Taq Readymix according to manufacturer's instructions (Sigma-Aldrich, Dorset, UK). PCR consisted of 40 cycles of 94° C. denaturation (15 s), 51-57° C. annealing (30 s; see table 1) and extension (30 s). The cycle threshold Ct was determined for each sample, and the average Ct of triplicate samples was calculated. The expression of each gene relative to Glyceraldehyde-3-Phosphate Dehydrogenase (GAPDH) was determined as ΔCt. A melt curve was constructed for each primer.

Immunohistochemistry

5 μm sections were de-paraffinised in xylene and rehydrated in ethanol. Antigen retrieval was performed in microwave MicroMed TT-Mega (Milestone, Sorisole, Italy) in 0.01 M citrate buffer pH 6.4. The staining procedure was performed using the Dako EnVision™+ System. Briefly, non-specific binding was blocked by incubation in 5% BSA in TBS-Tween 0.05% for 1 h and endogenous peroxidises were blocked with the hydrogen peroxide provided with the kit. Tissue sections were incubated with the primary antibody, either mouse anti-TFF3 (R&D Systems Europe Ltd, Abington, UK) or mouse anti-DDC (Protos Biotech Corporation, New York, USA) in 1% BSA in TBS-Tween 0.05% for 1 h at room temperature. The labelled polymer provided with the kit was then applied for 45 min followed by DAB substrate (DakoCytomation Ltd) for 10 min. Sections were counterstained with haematoxylin. A negative control was performed by omission of the primary antibody. Since the capsule sponge samples surface epithelium, quantification of immunohistochemical staining was restricted to the 4 top most layers of the mucosa. A mean of the extent and intensity was generated for each biopsy, reviewed at high magnification (×400), to generate an overall score for each slide. The intensity score was: 0 if absent, 1 for weak, 2 for medium and 3 for strong staining. The extent of staining was scored 1 for focal (1 focus of positive cells), 2 for multifocal (2 or more foci of positive, cells) and 3 for extensive (whole biopsy stained) staining.

Analysis

Figure 2:
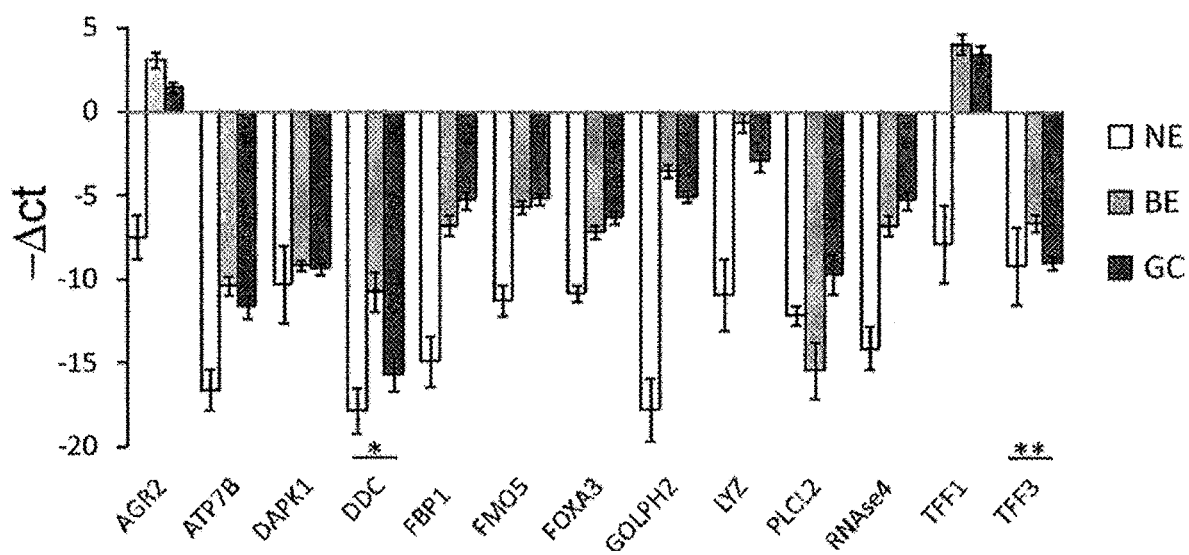
FIG. 2: mRNA expression of the putative genes identified. The Y axis represents the $-\Delta Ct$ (defined as $-(Ct_{target}-Ct_{GRAPH})$). The stars indicate statistical significance by one-way ANOVA (*$p=0.0339$ and **$p=0.0012$); only genes whose expression was significantly increased in BE compared to NE and GM are marked on this graph. In both cases, the genes were statistically upregulated in BE compared to NE and GC. In addition, AGR2, ATP7B, FBP1, FMO5, FOXA3, GOLPH2, LYZ, RNAase4 and TFF1 are statistically upregulated in BE (Barrett's oesophagus) and GC (gastric cardia) compared to NE (normal oesophagus).

The increased expression in BE compared to NE and GM was first confirmed at the mRNA level by real-time PCR in 10 histopathologically verified endoscopic biopsies from each tissue type. A suitable positive control could not be identified for FUT4 despite evaluating 3 primer pairs across 25 cells lines from different tissues. Validation of this target gene was therefore not taken any further. The expression of DAPK1 and PLCL2 was not statistically different between any groups. Most targets (AGR2, ATP7B, FBP1, FMO5, FOXA3, GOLPH2, LYZ, RNAase4 and TFF1) were statistically increased in BE compared to NE but were similar to GM (FIG. 2). However, both Dopa decarboxylase (DDC) and Trefoil factor 3 (TFF3) were statistically over-expressed in BE compared to NE (p<0.001 and p<0.01 respectively) and GM (p<0.01 and p<0.05 respectively).

Figure 3:
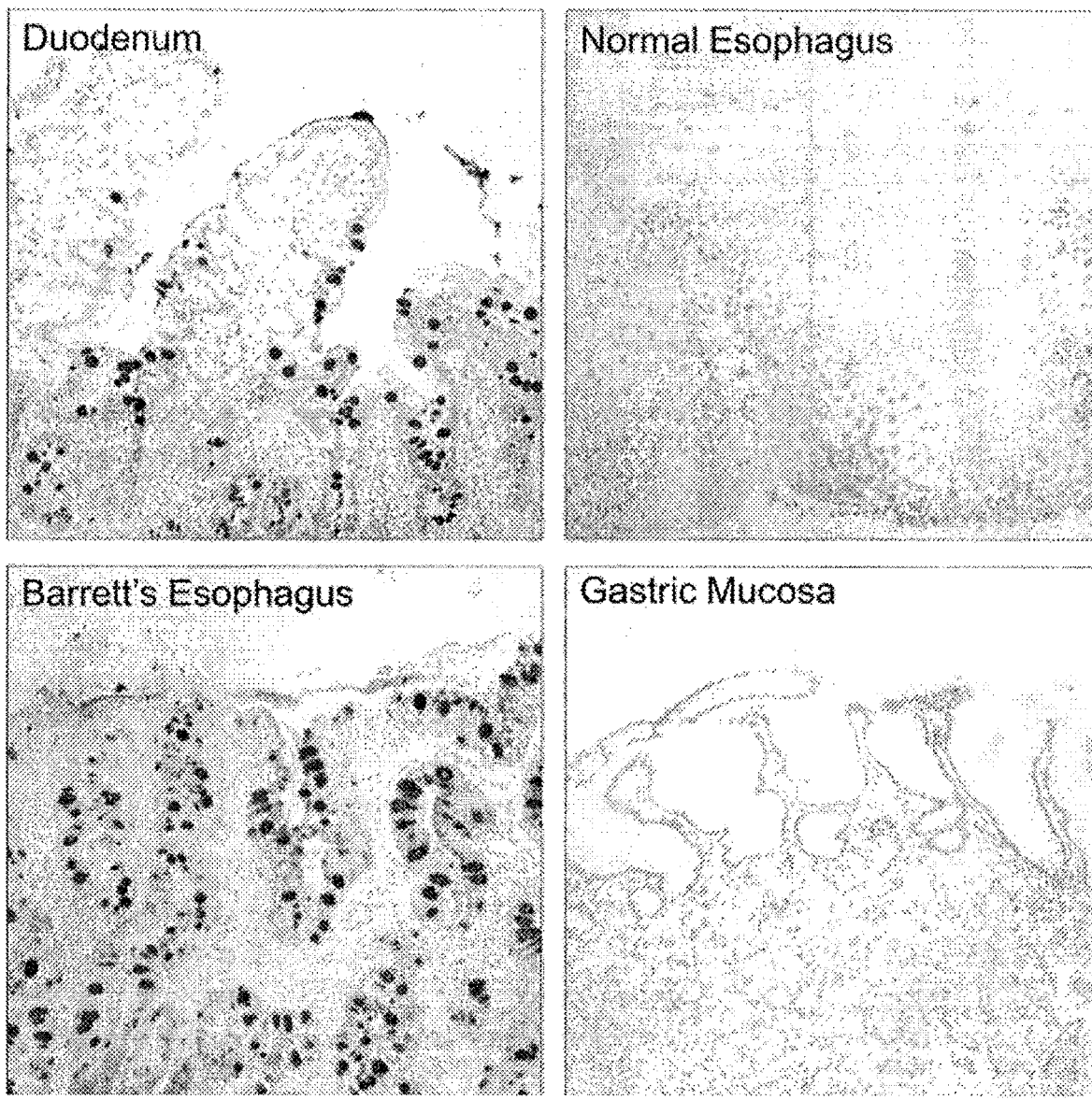
FIG. 3: Immunohistochemistry for TFF3 and DDC. Representative immunohistochemistry (×100) of TFF3 in the positive control duodenum, NE (normal oesophagus), BE (Barrett's oesophagus), GM (gastric mucosa).
Figure 4:
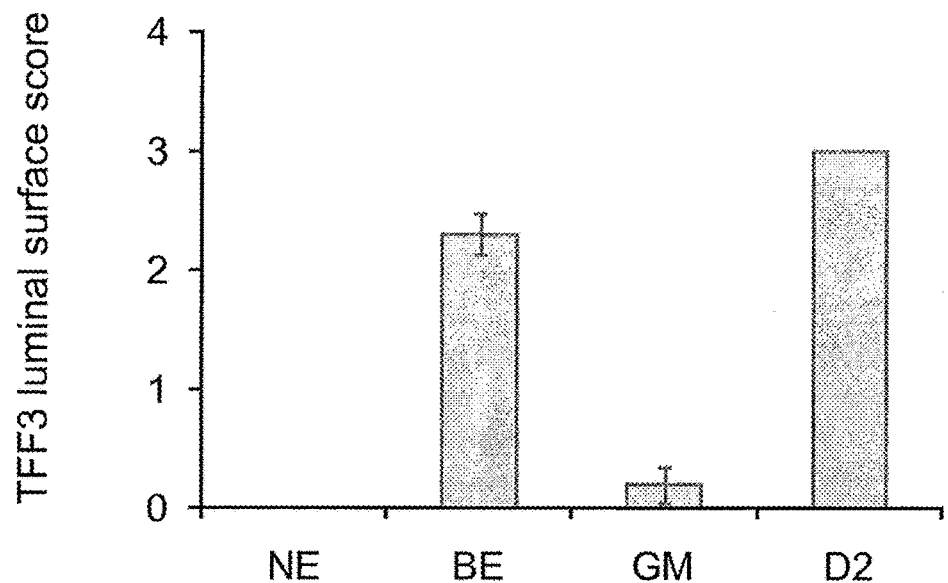
FIG. 4: Cumulative score for TFF3 in normal oesophagus, Barrett's oesophagus, stomach and duodenum. TFF3 is statistically over-expressed in BE (Barrett's oesophagus) compared to NE (normal oesophagus) and GM (gastric mucosa, $p<0.0001$).
Figure 5:
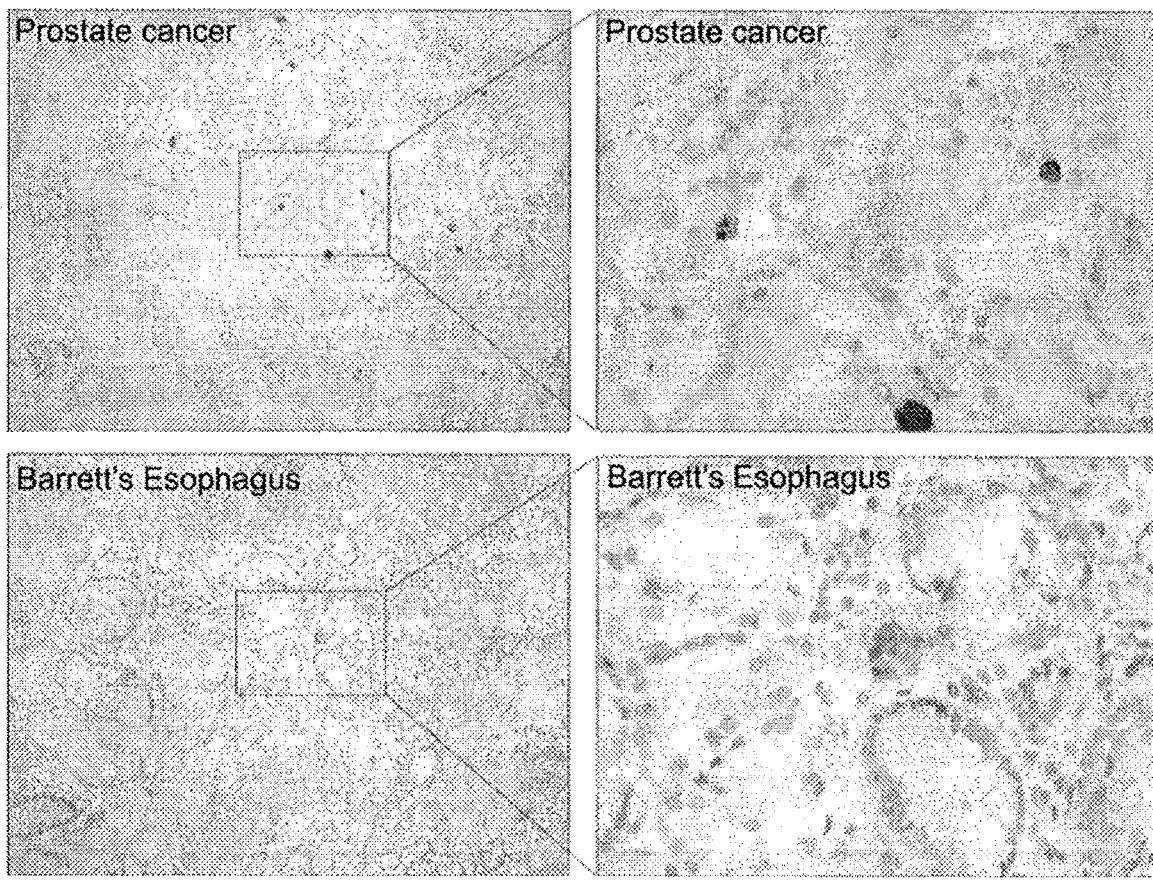
FIG. 5: Expression of DDC in prostate cancer, used as positive control, and in a positive Barrett's oesophagus biopsy (×100 and ×400 magnification).
Figure 6A:
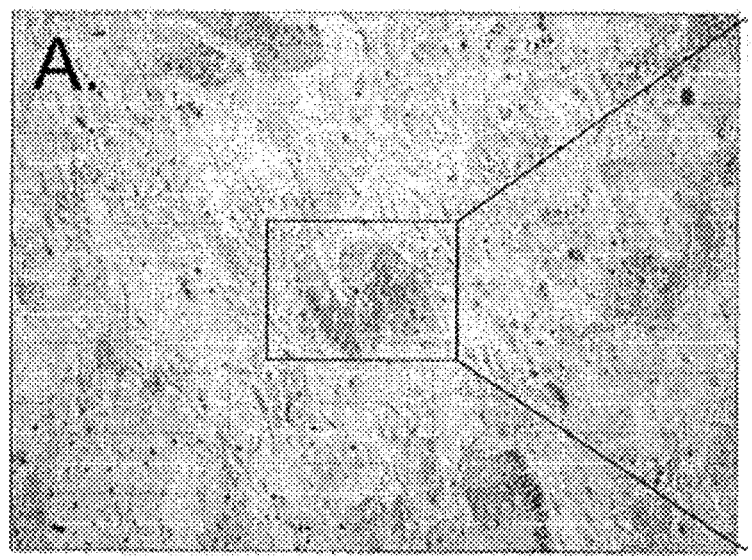
FIG. 6A-6D: Representative haematoxilin and eosin and TFF3 staining of a capsule specimen collected from a Barrett's patients (×100 and ×400 magnification). The black arrow indicates the typical circular appearance of TFF3 positivity and the red arrow indicates secreted TFF3 at the apical border of the Barrett's cells.
Figure 6B:
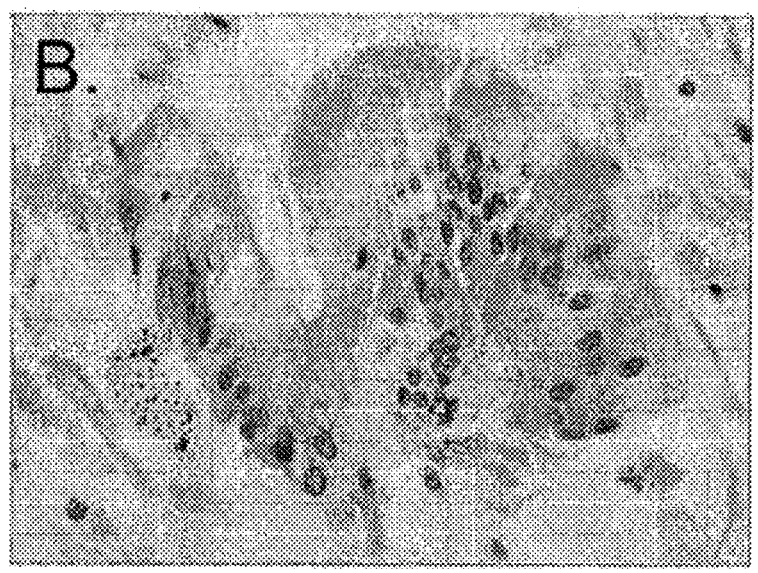
Figure 6C:
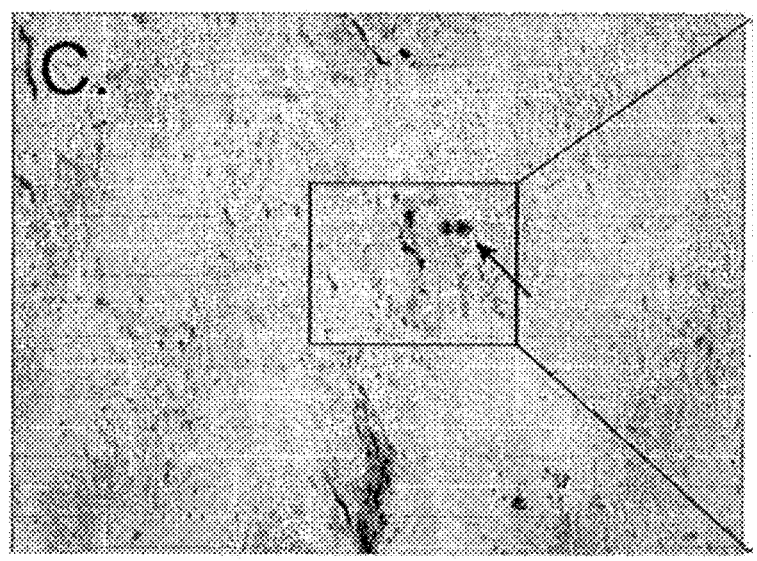
Figure 6D:
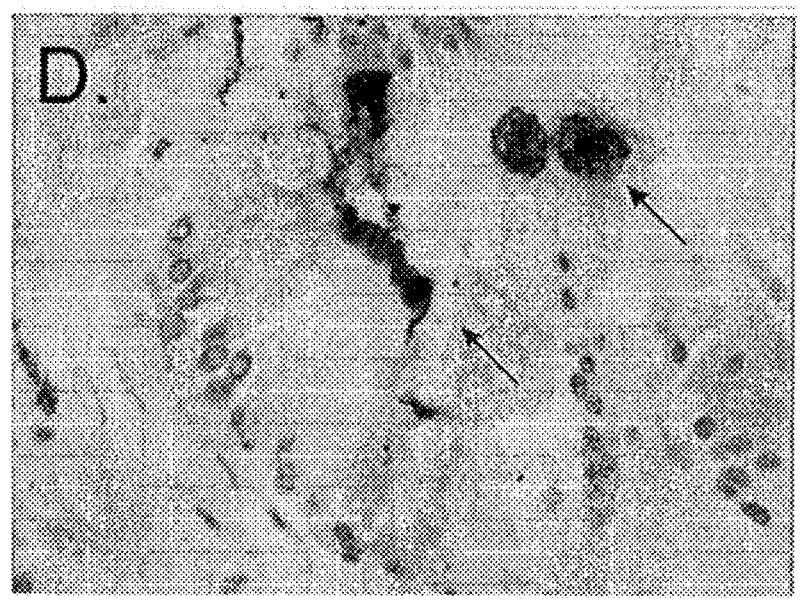

Since the capsule sponge specifically samples the uppermost layers of the mucosa, we then went on to validate the expression of TFF3 and DDC in paraffin-embedded section to address the epithelial localization of the antigen. TFF3 was expressed to high levels in BE compared to NE and GM both at the luminal surface and deeper within the tissue (FIGS. 3 and 4, p<0.001). TFF3 was therefore applicable to the capsule sponge which samples the surface layers of the gastric cardia and oesophagus. In contrast, DDC expression was only seen in 4/19 patients with BE and was absent in adjacent tissues (NE or GM) as expected. In the positive BE samples, DDC expression was very weak, limited to a small cluster of cells (less than 8) and localized towards the bottom of the crypts (FIG. 5).

Example 3: TFF3 Expression in Samples Collected with the Capsule Sponge

Since TFF3 fulfilled the necessary criteria, in that expression was restricted to the luminal surface of BE with no expression seen in gastric or normal squamous oesophageal tissues this was taken forward to the prospective capsule sponge screening study. TFF3 expression in specimens from 46 histologically confirmed BE patients were compared to 99 patients without BE.

Capsule Sponge Specimens

Following approval by the Cambridge Local Research Ethics Committee, 29 patients with known long-segment BE and 99 control patients (table 2), whose diagnosis was verified by endoscopy, were recruited. Only patients with a segment 3 cm were recruited to avoid erroneous diagnoses of hiatus hernia. Control patients were selected on the basis that they had reflux symptoms sufficient to require a prescription of acid-suppressant for a minimum of 3 months over the last 5 years but without diagnosis of BE. The patients were invited to attend a clinic at which they swallowed the sponge with a bolus of water and the capsule was left in place for 5 minutes before retrieval in preservative solution (SurePath, Burlington N.C., USA) as previously described [30].

Processing of the Capsule Sponge Specimens

Samples were left in preservative solution for a minimum of 1 hour. The samples were incubated for 30 minutes in Cytolyt® solution (Cytyc corporation), washed twice in PBS and pelleted at 1000 RPM for 5 minutes. The resulting pellet was re-suspended in 500 μL of plasma and thrombin (Diagnostic reagents, Oxford, UK) was then added in 10 μL increments until a clot formed. The clot was then placed in formalin for 24 h prior to processing into a paraffin block. The entire sample was cut in 5 μm sections to provide 20 slides. The first slide and every tenth slide were stained with H&E. Two sections representative of the whole sample, 10 slides apart, were stained for TFF3 as described above. A slide was scored positive for TFF3 if any cell was stained for TFF3.

Statistical Analysis

A Kruskal-Wallis one-way analysis of variance by ranks was performed to analyse differences in mRNA expression and expression of TFF3 at the luminal surface between the three groups using Prism (GraphPad Software). Specific differences were identified using a Dunn's post test. Microarray analysis was performed as described above.

One sample from a known Barrett's patient had a low cell yield and was excluded from the analysis. The staining was very intense (FIG. 6) and a dichotomous score (staining present or not) was used to maximize specificity. 36 out of 46 patients and 6 out of 99 control patients had a capsule sponge specimen positive for TFF3. A sensitivity of 78% (95% C1 64-89 (, specificity of 94% (95% C1 87-98) and a correct proportion of samples diagnosed of 89% (95% C1 83-94) were obtained. Representative haematoxilin and eaosin and TFF3 staining of a capsule specimen collected from a Barrett's patients (×100 and ×400 magnification) are shown in FIGS. 6A-6D.

We have demonstrated identification and use of a clinically relevant biomarker through the use of microarray data and careful validation. The biomarker identified using such an approach may be used in conjunction with the capsule sponge test to provide a cost-effective and acceptable screening test for BE.

REFERENCES

1. Brown L M, Devesa S S, Chow W H. Incidence of adenocarcinoma of the esophagus among white Americans by sex, stage, and age. J Natl Cancer Inst 2008; 100(16) 1184-7.
2. Lepage C, Rachet B, Jooste V, et al. Continuing Rapid Increase in Esophageal Adenocarcinoma in England and Wales. Am J Gastroenterol 2008.
3. Group MRCOCW. Surgical resection with or without preoperative chemotherapy in oesophageal cancer: a randomised controlled trial. Lancet 2002; 359:1727-33.
4. Chandrasoma P, Wickramasinghe K, Ma Y, et al. Is intestinal metaplasia a necessary precursor lesion for adenocarcinomas of the distal esophagus, gastroesophageal junction and gastric cardia? Diseases of the Esophagus 2007; 20(1):36-41.
5. Theisen J, Stein H J, Dittler H J, et al. Preoperative chemotherapy unmasks underlying Barrett's mucosa in patients with adenocarcinoma of the distal esophagus. Surg Endosc 2002; 16(4):671-3.
6. Schlansky B, Dimarino Jr A J, Loren D, et al. A survey of oesophageal cancer: pathology, stage and clinical presentation. Alimentary Pharmacology & Therapeutics 2006; 23(5):587-93.
7. Gerson L B, Shetler K, Triadafilopoulos G. Prevalence of Barrett's esophagus in asymptomatic individuals. Gastroenterology 2002, 123(2):461-7.
8. Rex D K, Cummings O W, Shaw M, et al. Screening for Barrett's esophagus in colonoscopy patients with and without heartburn. Gastroenterology 2003, 125(6): 1670-7.
9. Ward E M, Wolfsen H C, Achem S R, et al. Barrett's Esophagus Is Common in Older Men and Women Undergoing Screening Colonoscopy Regardless of Reflux Symptoms. The American Journal of Gastroenterology 2006; 101(1):12-7.
10. Pera M. Trends in Incidence and Prevalence of Specialized Intestinal Metaplasia, Barrett's Esophagus, and Adenocarcinoma of the Gastroesophageal Junction. World Journal of Surgery 2003; 27(9):999-1006.
11. Ronkainen J, Aro P, Storskrubb T, et al. Prevalence of Barrett's esophagus in the general population: an endoscopic study. Gastroenterology 2005; 129(6) 1 825-31.
12. Streitz J M, Jr., Andrews C W, Jr., Ellis F H, Jr. Endoscopic surveillance of Barrett's esophagus. Does it help? J Thorac Cardiovasc Surg 1993; 105(3):383-7; discussion 7-8.
13. Peters J H, Clark G W, Ireland A P, et al. Outcome of adenocarcinoma arising in Barrett's esophagus in endoscopically surveyed and nonsurveyed patients. J Thorac Cardiovasc Surg 1994; 108(5):813-21; discussion 21-2.
14. van Sandick J W, van Lanschot J J, Kuiken B W, et al. Impact of endoscopic biopsy surveillance of Barrett's oesophagus on pathological stage and clinical outcome of Barrett's carcinoma. Gut 1998; 43(2):216-22.
15. Incarbone R, Bonavina L, Saino G, et al. Outcome of esophageal adenocarcinoma detected during endoscopic biopsy surveillance for Barrett's esophagus. Surg Endosc 2002; 16(2):263-6.
16. Ferguson M K, Durkin A. Long-term survival after esophagectomy for Barrett's adenocarcinoma in endoscopically surveyed and nonsurveyed patients. J Gastrointest Surg 2002; 6(1):29-35; discussion 6.
17. Fountoulakis A, Zafirellis K D, Dolan K, et al. Effect of surveillance of Barrett's oesophagus on the clinical outcome of oesophageal cancer. Br J Surg 2004; 91(8):997-1003.
18. Corley D A, Levin T R, Habel L A, et al. Surveillance and survival in Barrett's adenocarcinomas: a population-based study. Gastroenterology 2002; 122(3):633-40.
19. Reddymasu S C, Sharma P. Advances in endoscopic imaging of the esophagus. Gastroenterol Clin North Am 2008; 37(4):763-74.
20. Mehta S, Johnson I T, Rhodes M. Systematic review: the chemoprevention of oesophageal adenocarcinoma. Alimentary Pharmacology & Therapeutics 2005, 22(9):759-68.
21. Ilyas S, DeMars C, Buttar N. Chemoprevention in Barrett's Esophagus. Journal of Gastrointestinal Cancer 2007; 38(1) 1-9.
22. BSG. Guidelines for the diagnosis and management of Barrett's columnar-lined oesophagus. http://wwwbsgorguk 2005.
23. Fennerty M B, DiTomasso J, Morales T G, et al. Screening for Barrett's esophagus by balloon cytology. Am J Gastroenterol 1995; 90(8) 1230-2.
24. Falk G W, Chittajallu R, Goldblum J R, et al. Surveillance of patients with Barrett's esophagus for dysplasia and cancer with balloon cytology. Gastroenterology 1997; 112(6):1787-97.
25. Spechler S J. Barrett's esophagus: should we brush off this ballooning problem? Gastroenterology 1997, 112(6): 2138-42.
26. Gerson L B, Edson R, Lavori P W, et al. Use of a simple symptom questionnaire to predict Barrett's esophagus in patients with symptoms of gastroesophageal reflux. Am J Gastroenterol 2001; 96(7):2005-12.
27. Locke G R, Talley N J, Weaver A L, et al. A new questionnaire for gastroesophageal reflux disease. Mayo Clin Proc 1994; 69(6):539-47.
28. Sharma P, Wani S, Rastogi A, et al. The Diagnostic Accuracy of Esophageal Capsule Endoscopy in Patients With Gastroesophageal Reflux Disease and Barrett's Esophagus: A Blinded, Prospective Study. The American Journal of Gastroenterology 2008, 103(3):525-32.
29. Ramirez F C, Akins R, Shaukat M. Screening of Barrett's esophagus with string-capsule endoscopy: a prospective blinded study of 100 consecutive patients using histology as the criterion standard. Gastrointestinal Endoscopy In Press, Corrected Proof.
30. Lao-Sirieix P, Rous B, O'Donovan M, et al. Non-endoscopic immunocytological screening test for Barrett's oesophagus. Gut 2007; 56(7):1 033-4.
31. Lao-Sirieix P, Kadri S, Debiram I, et al. Non-endoscopic screening for Barrett's oesophagus using the capsule sponge is well tolerated and allows tissue architecture to be retained. J Clin Gastroenterol 2008; 42(S1):Abstract.
32. Hao Y, Triadafilopoulos G, Sahbaie P, et al. Gene expression profiling reveals stromal genes expressed in common between Barrett's esophagus and adenocarcinoma. Gastroenterology 2006; 131(3):925-33.
33. Boussioutas A, Li H, Liu J, et al. Distinctive patterns of gene expression in premalignant gastric mucosa and gastric cancer. Cancer Res 2003; 63(10):2569-77.
34. Greenawalt D M, Duong C, Smyth G K, et al. Gene expression profiling of esophageal cancer: comparative analysis of Barrett's esophagus, adenocarcinoma, and squamous cell carcinoma. Int J Cancer 2007; 120(9): 1914-21.
35. Paik S, Shak S, Tang G, et al. A multigene assay to predict recurrence of tamoxifen-treated, node-negative breast cancer. N Engl J Med 2004; 351(27):2817-26.
36. Paik S, Tang G, Shak S, et al. Gene expression and benefit of chemotherapy in women with node-negative, estrogen receptor-positive breast cancer. J Clin Oncol 2006; 24(23):3726-34.
37. van 't Veer L J, Dai H, van de Vijver M J, et al. Gene expression profiling predicts clinical outcome of breast cancer. Nature 2002; 415(6871):530-6.
38. van Baal J W P M, Diks S H, Wanders R J A, et al. Comparison of Kinome Profiles of Barrett's Esophagus with Normal Squamous Esophagus and Normal Gastric Cardia. Cancer Res 2006; 66(24):11605-12.
39. van Baal J W, Milano F, Rygiel A M, et al. A comparative analysis by SAGE of gene expression profiles of Barrett's esophagus, normal squamous esophagus, and gastric cardia. Gastroenterology 2005; 129(4):1274-81.
40. Dignass A, Lynch-Devaney K, Kindon H, et al. Trefoil peptides promote epithelial migration through a transforming growth factor beta-independent pathway. J din Invest 1994; 94(1):376-83.
41. Wong W M, Poulsom R, Wright N A. Trefoil peptides. Gut 1999; 44(6):890-5.
42. Hoffmann W, Jagla W, Wiede A. Molecular medicine of TFF-peptides: from gut to brain. Histol Histopathol 2001; 13(1):319-34.
43. Baus-Loncar M, Kayademir T, Takaishi S, et al. Trefoil factors. Cellular and Molecular Life Sciences (CMLS) 2005; 62(24):2947-55.
44. Kouznetsova I, Kalinski T, Peitz U, et al. Localization of TFF3 peptide in human esophageal submucosal glands and gastric cardia: differentiation of two types of gastric pit cells along the rostro-caudal axis. Cell and Tissue Research 2007; 328(2):365-74.
45. Peitz U, Kouznetsova I, Wex T, et al. TFF3 expression at the esophagogastric junction is increased in gastro-esophageal reflux disease (GERD). Peptides 2004; 25(5): 771-7.
46. Shimada T, Koike T, Yamagata M, et al. Regulation of TFF3 expression by homeodomain protein CDX2. Regulatory Peptides 2007; 140(1-2):81-7.
47. Takano T, Yamada H. Trefoil factor 3 (TFF3): a promising indicator for diagnosing thyroid follicular carcinoma. Endocr J 2008; doi:10.1507/endocrj.K08E-105.
48. Bryson P C, Shores C G, Hart C, et al. Immunohistochemical distinction of follicular adenomas and follicular carcinomas. Arch Otolaryngol Head Neck Surg 2008; 134(6):581-6.
49. Bignotti E, Ravaggi A, Tassi R A, et al. Trefoil factor 3: a novel serum marker identified by gene expression profiling in high-grade endometrial carcinomas. Br J Cancer 2008; 99(5):768-73.
50. Christenson J G, Dairman W, Udenfriend S. On the identity of DOPA decarboxylase and 5-hydroxytryptophan decaroxylase. Proc Nati Acad Sci USA 1972; 69(2): 343-7.
51. Eldrup E, Clausen N, Scherling B, et al. Evaluation of plasma 3,4-dihydroxyphenylacetic acid (DOPAC) and plasma 3,4-dihydroxyphenylalanine (DOPA) as tumor markers in children with neuroblastoma. Scand J Clin Lab Invest 2001; 61(6):479-90.
52. Gilbert J, Haber M, Bordow S B, et al. Use of tumor-specific gene expression for the differential diagnosis of neuroblastoma from other pediatric small round-cell malignancies. Am J Pathol 1999; 155(1):17-21.
53. Jensen S M, Gazdar A F, Cuttitta F, et al. A comparison of synaptophysin, chromogranin, and L-dopa decarboxylase as markers for neuroendocrine differentiation in lung cancer cell lines. Cancer Res 1990; 50(18):6068-74.
54. Avgeris M, Koutalellis G, Fragoulis E G, et al. Expression analysis and clinical utility of L-Dopa decarboxylase (DDC) in prostate cancer. Clin Biochem 2008.
55. Sakakura C, Takemura M, Hagiwara A, et al. Overexpression of dopa decarboxylase in peritoneal dissemination of gastric cancer and its potential as a novel marker for the detection of peritoneal micrometastases with real-time RT-PCR. Br J Cancer 2004; 90(3):665-71.
56. Trager C, Vernby A, Kullman A, et al. mRNAs of tyrosine hydroxylase and dopa decarboxylase but not of GD2 synthase are specific for neuroblastoma minimal disease and predicts outcome for children with high-risk disease when measured at diagnosis. Int J Cancer 2008.
57. Wang K K, Sampliner R E. Updated Guidelines 2008 for the Diagnosis, Surveillance and Therapy of Barrett's Esophagus Am J Gastroenterol 2008; 103:788-97.
58. Donaldson L. On the State of Public Health: Annual Report of the Chief Medical Officer 2007. 2008; http://www.dh.gov.uk/en/Publicationsandstatistics/Publications/Annual Reports/DH_086 176: Accessed 20 Jan. 2009.
59. Bunting P S. Screening for prostate cancer with prostate-specific antigen: beware the biases. Clin Chim Acta 2002; 315(1-2):71-97.
60. Towler B, Irwig L, Glasziou P, et al. A systematic review of the effects of screening for colorectal cancer using the faecal occult blood test, hemoccult. Bmj 1998; 317(7158): 559-65.
61. Nanda K, McCrory D C, Myers E R, et al. Accuracy of the Papanicolaou test in screening for and follow-up of cervical cytologic abnormalities: a systematic review. Ann Intern Med 2000; 132(10):810-9.

Example 4: BEST2: Evaluation of a Non-Endoscopic Immunocytological Device (Cytosponge) for Barrett's Esophagus Screening Via a Case-Control Study and a Screening Trial in Primary Care Background Incidence rates of oesophageal adenocarcinoma (AC) have increased 6 fold in the last 30 years [1] and the 5 year survival remains less than 14% [2]. For these reasons, both Cancer Research UK and the Chief Medical Officer have highlighted this disease as a strategic priority and recommended that research should be supported to explore minimally invasive screening tests [3]. The ability to detect BE is a critical screening question because this is the precursor for oesophageal adenocarcinoma. Hitherto the utility of screening for BE has been questionable given the lack of treatment options. However, there has been rapid advancement in technologies such as endoscopic mucosal resection and radiofrequency ablation with randomised controlled trial evidence to support their efficacy [4, 5]. In addition, chemoprevention measures are being evaluated in a large CRUK funded trial (AspECT). Therefore screening-detected cases of BE could potentially be coupled to interventions to prevent AC thus avoiding the need for oesophagectomy which has significant mortality and morbidity [2].

Any screening test needs to be simple, safe, precise, validated and acceptable to the population [6]. The current gold-standard endoscopic diagnosis is invasive, technical and expensive. Development of ultrathin transnasal endoscopy may improve acceptability; however it remains an invasive, expensive test requiring technical expertise [7, 8]. Wireless video capsule endoscopy has a high sensitivity [9]; but is also high-tech, expensive and does not permit tissue sampling. Previous attempts to develop non-endoscopic cytological screening tests, such as balloon cytology have failed [10].

Development of the Cytosponge Test and Pilot Data

We have developed an MHRA approved (CI/2007/0053) non-endoscopic device called a Cytosponge to screen for BE (FIG. 1A). It consists of an expandable, spherical mesh which is attached to a string and contained within a soluble capsule. 3-5 minutes after swallowing, the mesh can be retrieved by pulling on the string. After placing into preservative fluid the specimen is processed for biomarker evaluation (FIG. 1B). In a case:control study the most promising BE biomarkers were an antibody raised against the proliferation marker Mcm2; and a mucin characteristic of the intestinal metaplastic phenotype TFF3 [11, 12]. Protein based assays were chosen for their applicability to routine clinical diagnostic pathology laboratories.

Figure 7A:
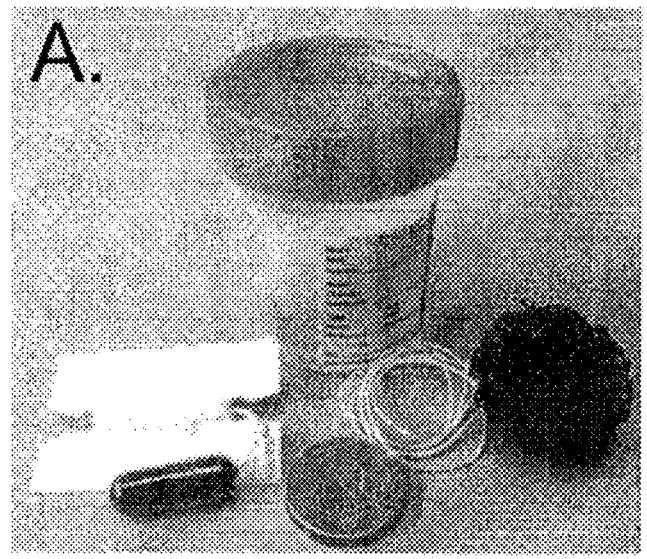
FIG. 7A-7B shows: Cytosponge within the capsule and expanded (A) and representative picture of positive TFF3 staining in a sample from a patient with BE (B).
Figure 7B:
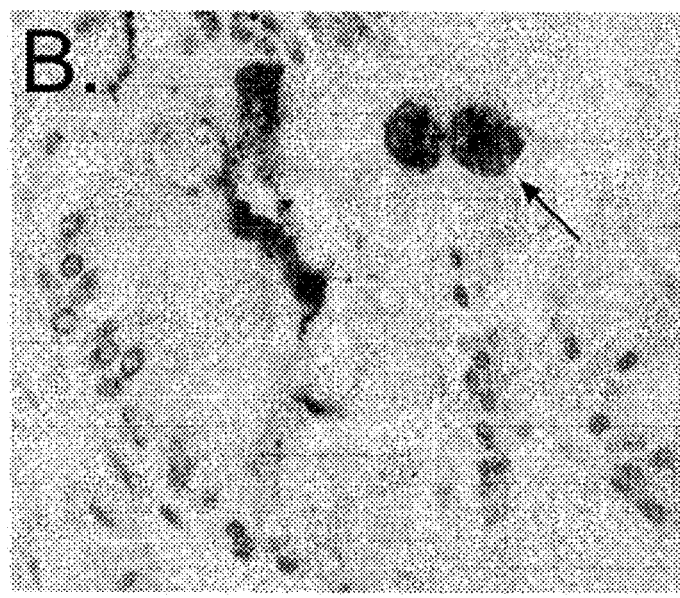

Next we examined the feasibility and acceptability of using the Cytosponge in primary care (www.beststudy.org.uk), [13, 14]. To date 491 patients (mean age, 62 years with a M:F ratio of 0.8:1) with a history of reflux disease have been recruited from 2,602 patients from 11 practices giving an uptake of 18.9% in line with previous primary care endoscopic studies [15, 16]. Only 3/491 (<0.01%) were unable to swallow the device and there were no serious adverse events. Cytosponge results were compared with endoscopy as the gold-standard with a compliance of 92%. In this population the prevalence of BE containing specialized intestinal metaplasia was 2.2%, in keeping with other non-UK population data [16-19]. Although not powered to determine accuracy of the test as a primary outcome measure, the Cytosponge test detected BE (TFF3) with a sensitivity and specificity of 90% and 95% respectively. Hence, this pilot study has demonstrated that the Cytosponge is simple and safe enough to be applied to the primary care setting. Further data are required to validate the test and provide robust data on its precision. See FIG. 7. FIG. 7A shows a Cytosponge within the capsule and expanded. FIG. 7B shows a representative picture of positive TFF3 staining in a sample from a patient with BE.

Biomarkers for Risk Stratification

BE progresses to adenocarcinoma via a metaplasia-dysplasia adenocarcinoma sequence at a rate of 0.6% per year [20]. Therefore, in order to avoid placing an undue burden on endoscopic surveillance, the ideal screening test should also risk stratify patients according to their likelihood of progressing to AC. This is currently assessed by the histopathological assessment of the degree of dysplasia on biopsies but more objective molecular biomarkers are emerging.

DNA ploidy, p16 and p53 abnormalities are currently the best predictors of cancer progression with a relative risk of up to 38.7 (95% CI 10.8-138.5; p<0.001) [21, 22]. Whilst the assays employed for these analyses are highly technical, image cytometric analysis of ploidy [23, 24] and immunohistochemical detection of p53 abnormalities are promising [25]. In addition, cyclin A and MCM2 detect >90% high grade and adenocarcinoma cases [12, 26]. Since these markers specifically detect epithelial cell surface abnormalities using routine immunohistochemistry they are ideally suited to the Cytosponge. Finally, a panel of 8 methylated genes assayed from paraffin embedded specimens have been validated in a double blind study [27, 28].

Hypothesis

We hypothesise that the Cytosponge test could be used as a clinical screening test in primary care, which when coupled with appropriate biomarkers could also diagnose the degree of dysplasia.

Proposed Design

Figure 8:
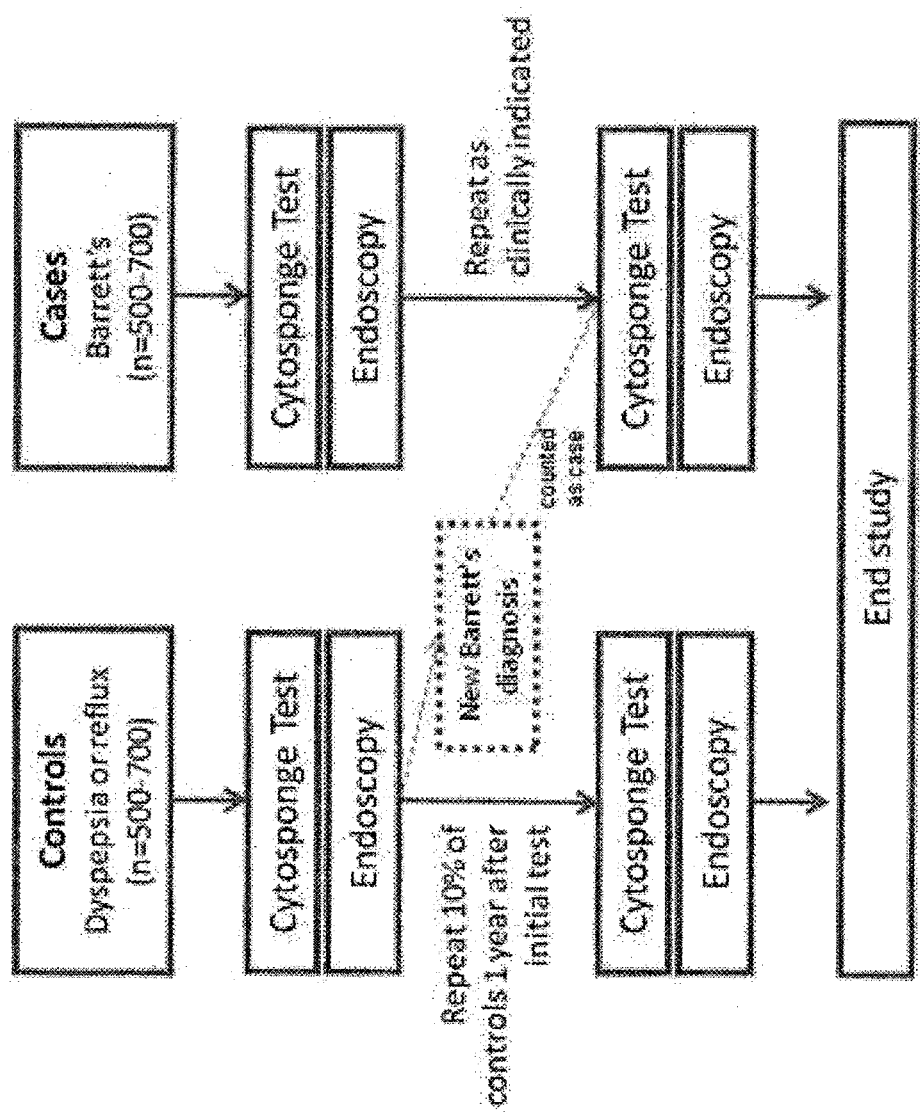
FIG. 8 shows a diagram.

A screening trial together with a Case:Control study will recruit patients from three different populations in order to determine the performance characteristics of the Cytosponge for diagnosing BE compared with endoscopy, including specificity (from controls) and sensitivity (from cases) and numbers needed to test (from the primary-care based trial). The project design was driven by the need to: a) maximise the information gained with regards to both diagnosis of BE and presence of dysplasia and b) to avoid endoscoping individuals with a negative Cytosponge result who would otherwise not have sought medical care. The design is summarised in FIG. 8.

1. Screening Trial: Primary Care

The primary clinical outcome measure for the screening trial will be histologically confirmed BE.

Setting and Practice Recruitment 2,500 individuals with symptomatic reflux will be identified and invited to swallow the Cytosponge via the East of England (EoE) Primary Care Research Network (PCRN). From the 20% acceptance rate in the BEST pilot study we would require a combined practice population of about 500,000 people, from 55-60 practices which is possible via the EoE PCRN. All interested surgeries will be visited by the study staff to discuss the purpose and logistics of the study including a video of a volunteer swallowing the Cytosponge.

Inclusion and Exclusion Criteria

Individuals 50-70 years of age who have required an anti-reflux prescription for >3 months over the past 5 years will be identified from a search of the electronic drug prescribing data base by the practice staff. Patients who had upper GI endoscopy in the past year, those who are known to have BE and individuals unable to give informed consent will be excluded.

Appointment Process

The subject will provide demographic information which will be entered by the study nurse using a custom-made database accessed via the web. Baseline information will be collected (weight, height, waist:hip ratio) and patients will complete a validated reflux questionnaire [29]. The Cytosponge will be administered by the study nurse. Following the test and whilst still in the surgery the subject will complete baseline psychological measures (see section on QOL).

Patients with a positive test (defined on the basis of any TFF3 positivity) will be invited for an endoscopy within 6 weeks. Any BE visible endoscopically will be confirmed with biopsies for standard histopathological evaluation. Further psychological questionnaire measures will be sent by post at days 7 and 90.

A subgroup of individuals (1500 invited to recruit 1200 over the duration of the study) with a negative Cytosponge test will be offered a repeat test (either 1 or 2 years later) and as in the first screening test individuals testing positive will be endoscoped and psychological questionnaires completed.

2. Case-Control Study Secondary Care

The primary clinical outcome measure for the case-control study will be positive staining for TFF3.

Recruitment 500 individuals with known BE (cases) undergoing surveillance, including those referred for further evaluation and management of high grade dysplasia (HGD) will be recruited. 500 individuals referred by their GP for an endoscopic evaluation of dyspepsia (controls) will also be invited to attend. The timeline of the study is summarized in FIGS. 9A-9C.

Inclusion and Exclusion Criteria

Any patient clinically fit for an endoscopy is eligible to take part. Individuals with dysphagia will be excluded. Patients must be able to provide informed consent.

Appointment Process

Baseline demographic and symptom information will be collected as described from the screening trial. After obtaining informed consent the Cytosponge will be administered by the study nurse prior to their clinically indicated endoscopy. Any newly endoscopically diagnosed BE in the control arms will be biopsied as for the screening trial and these patients will be then be considered as cases. For patients undergoing surveillance, biopsies will be taken according to the Seattle protocol and graded according to the Vienna classification system [30]. Prior to biopsies, an endoscopically directed brushing of Barrett's mucosa will be taken for biomarker evaluation to compare with the Cytosponge specimen as previously described [12, 26]. Psychological questionnaire measures will be obtained at days 0, 7 and 90.

Sample Processing from Screening and Case Control Arms

All Cytosponge specimens will be processed as previously described [11] and evaluated for the Barrett's diagnostic biomarkers (TFF3) using a DAKO autostainer according to GCP standards. Samples will be scored in a binary fashion (positive or negative) as already optimised from the pilot study. A screener will identify areas of interest for the expert GI cytologist (M O'D) to verify.

Patients with a positive result for the Barrett's diagnostic biomarkers will have additional sections cut for risk stratification biomarkers. Mcm2, cyclin A and TP53 can be performed on the DAKO autostainer. The ploidy analysis will be performed using image cytometry [23], (Lovat laboratory) and methylation will be performed using methylation specific PCR [27], (Fitzgerald laboratory). The biomarkers will be scored according to previously optimised protocols [11, 12, 23, 26]. These data will be compared to the degree of dysplasia determined from endoscopic biopsies.

Primary and Secondary Clinical Outcomes from Screening and Case Control Arms:

Primary Outcome:
Performance characteristics of the Cytosponge test for diagnosing BE compared with endoscopy, including specificity (from controls) and sensitivity (from cases) and numbers needed to test (from the primary-care based screening trial).

Secondary Outcomes:
Differential sensitivity of screening BE with high-grade dysplasia compared to non-dysplastic BE.
For patients with BE, (screened and surveillance patients) we will determine the ability of Cytosponge biomarkers to risk stratify patients in comparison with dysplasia grade obtained from endoscopic biopsies.
Preliminary data on numbers needed to test to detect one case of BE after an interval of one and two years following a negative screen. These data will be key to determining the screening frequency for future trials.

Logistics of high-throughput sample processing and automated analysis of Cytosponge specimens for use in routine NHS or other health care settings.
Recruitment rates and acceptability in the primary care-trial will be determined and compared between different socio-demographic groups.
Potential for Bolt-on Studies and Translational Research:
Surplus material from screening and surveillance populations will be used for testing emerging biomarkers
Longer term (20 years), the incidence of oesophageal adenocarcinoma in individuals with positive versus negative test will be available through flagging with the ECRiC Eastern Cancer Registry and Information Centre.
Opportunity to re-contact participants in the screening trial in relation to other cancer prevention behavioural interventions e.g. smoking cessation, obesity reduction or chemoprevention.

Sample Size Estimation:

The main goal is to obtain accurate estimates of the screening parameters (sensitivity, specificity, positive predictive value and numbers needed to screen to detect one case). We therefore aim to estimate specificity with 95% confidence intervals of approximately +/−1% and sensitivity with intervals of +/−2.5%. Where testing has been considered (such as comparing Barrett's with and without high grade dysplasia, or comparing results at entry and 12 or 24 months later) we have aimed for between 80% and 90% power. Details sample size considerations are available from Peter Sasieni on request.

Additional Information on Study Logistics:

A full-time study co-ordinator will be based in Cambridge and work closely with the Cancer Prevention Trials Unit.

1) Screening Trial: Primary Care

Three full-time research nurses based in EoE will work in parallel to recruit participants. The NIHR primary care network is being approached for funding support for research nurses. Twice monthly endoscopy, in primary-care associated units in proximity to the practices concerned, will be performed by a Joint Advisory Board (JAG) accredited upper GI endoscopist. Appointments will be made by a full-time study booking clerk working with the study co-ordinator in Cambridge.

2) Case:Control Study: Secondary Care

The patients will be recruited form 3 tertiary referral centres (Cambridge, Nottingham and UCLH) with expertise in BE (over 700 patients per year of which 135 have HGD). These centres all have research nurses who will have dedicated time for this study (5 sessions per week).

Quality of Life and Economic Evaluations

To measure the impact of screening on psycho-social well-being participants will complete the validated Impact of Events Scale and the Short Form STAI/TRAIT anxiety questionnaires before the test, 7 and 90 days later. Health state utility data using the EQ-5D as recommended by NICE [31]) and resource use data (diagnostic and therapeutic endoscopy, anti-reflux medication, surgery) will be collected. This information will subsequently be used to populate a Markov process model to estimate the cost per QALY from a UK perspective to compare to existing data concerning endoscopic screening for BE [32]. Funding is not required for this part of the proposal. A parallel application will be made to the NIHR to fund quality of life and health economic studies. See FIG. 10.

Preparation, staining and reading of slides from the Cytosponge will be done blinded to the route by which the patient was recruited (screening, case, potential control) and to any endoscopy findings. Similarly, BE histology will be evaluated blinded to the reason for endoscopy (surveillance or triage of a positive screen). Interim analyses will be performed at the end of the first and second year of the study.

The data will be analysed using standard techniques for screening studies. In the screening trial adjustments will be made for the lack of endoscopy both in those who screen negative and more particularly in those who screen positive but subsequently fail to comply with recommended follow-up. A detailed statistical analysis plan will be produced in conjunction with PS before the data are examined. Exploratory analyses will explore factors (such as ages, sex and obesity) affecting specificity and disease prevalence in the screening trial.

Clinical Governance

The Cancer Prevention Clinical Trials Unit will ensure clinical governance standards are met and will advise on practical issues. The TFF3 biomarker assays will be performed in clinical histopathological laboratories to GCP standards. All clinical decisions concerning interventions for BE associated dysplasia will be made on the basis of the histopathological grading of the endoscopic biopsies according to standard clinical practice without reference to biomarker data.

An advisory board will meet annually during the course of the study to: oversee and advise, serve as a dissemination vehicle to other researchers and policy makers and to serve as a 'springboard' for subsequent epidemiological and clinical collaborations.

Anticipated Use of Study Results to Inform Clinical Decision Making

Increasing public awareness and an increasing incidence of AC mean that it is timely to conduct work to inform policy decisions about a national BE screening programme. In the future the results from this study could lead on to a RCT to compare the effects of screening, coupled with endoscopic treatment for those individuals diagnosed with high risk BE, compared with no screening on mortality form AC.

REFERENCES

1. Brown, L M, Devesa, S S, and Chow, W H, Incidence of adenocarcinoma of the esophagus among white Americans by sex, stage, and age. (2008) J Natl Cancer Inst 100(16), 1184-1187.
2. Medical Research Council Oesophageal Cancer Working Group, Surgical resection with or without preoperative chemotherapy in oesophageal cancer: a randomised controlled trial. (2002) Lancet 359(9319), 1727-1733.
3. Donaldson, L, Chapter 6: A pathological concern: Understanding the rise in oesophageal cancer. (2007) Annual Report of the Chief Medical Officer, http://www.dh.gov.uk/en/Publicationsandstatistics/Publications/AnnualReports/DH_0861 76.
4. Shaheen, N J, Sharma, P, Overholt, B F, et al., Radiofrequency ablation in Barrett's esophagus with dysplasia. (2009) N Engl J Med 360(22), 2277-2288.
5. Pouw, R E, Wirths, K, Eisendrath, P, et al., Efficacy of Radiofrequency Ablation Combined With Endoscopic Resection for Barrett's Esophagus With Early Neoplasia. (2009) Clin Gastroenterol Hepatol.
6. UK National Screening Commitee, Criteria for appraising the viability, effectiveness and appropriateness of a screening programme. (2009) http://www.screening.nhs.uk/criteria.
7. Saeian, K, Staff, D M, Vasilopoulos, S, et al., Unsedated transnasal endoscopy accurately detects Barrett's metaplasia and dysplasia. (2002) Gastrointest Endosc 56(4), 472-478.
8. Dumortier, J, Napoleon, B, Hedelius, F, et al., Unsedated transnasal EGD in daily practice: results with 1100 consecutive patients. (2003) Gastrointest Endosc 57(2), 198-204.
9. Ramirez, F C, Akins, R, and Shaukat, M, Screening of Barrett's esophagus with string-capsule endoscopy: a prospective blinded study of 100 consecutive patients using histology as the criterion standard. (2008) Gastrointestinal Endoscopy 68(1), 25-31.
10. Fennerty, M B, DiTomasso, J, Morales, T G, et al., Screening for Barrett's esophagus by balloon cytology. (1995) Am J Gastroenterol 90(8), 1230-1232.
11. Lao-Sirieix, P, Boussioutas, A, Kadri, S R, et al., Non-endoscopic screening biomarkers for Barrett's oesophagus: from microarray analysis to the clinic. (2009) Gut 58(11), 1451-1459.
12. Sirieix, P, O'Donovan, M, Brown, J, et al., Surface expression of mini chromosome maintenance proteins provides a novel method for detecting patients at risk for developing adeocarcinoma in Barrett's oesophagus. (2003) Clin Cancer Res.
13. Kadri, S R, Debiram, I, Lao-Sirieix, P, et al., A pilot feasibility study of screening for Barrett's esophagus with a novel non-endoscopic capsule sponge device in a primary care setting. (2009) Gastroenterology 136 (Suppl 1), T1877.
14. Kadri, S R, Lao-Sirieix, P, O'Donovan, M, et al., Non-endoscopic screening for Barrett's oesophagus in the community. (In preparation).
15. Wong, A, Lovat, L, Burnham, R W, et al., Large-scale prospective study reveals novel risk factors for Barrett's oesophagus. (2007) Gut 56(supp II), A8.
16. Ronkainen, J, Aro, P, Storskrubb, T, et al., Prevalence of Barrett's esophagus in the general population: an endoscopic study. (2005) Gastroenterology 129(6), 1825-1831.
17. Gerson, L B, Shetler, K, and Triadafilopoulos, G, Prevalence of Barrett's esophagus in asymptomatic individuals. (2002) Gastroenterology 123(2), 461-467.
18. Rex, D K, Cummings, O W, Shaw, M, et al., Screening for Barrett's esophagus in colonoscopy patients with and without heartburn. (2003) Gastroenterology 125(6), 1670-1677.
19. Ward, E M, Wolfsen, H C, Achem, S R, et al., Barrett's Esophagus Is Common in Older Men and Women Undergoing Screening Colonoscopy Regardless of Reflux Symptoms. (2006) The American Journal of Gastroenterology 101(1), 12-17.
20. Sikkema, M, de Jonge, P J, Steyerberg, E W, et al., Risk of Esophageal Adenocarcinoma and Mortality in Patients With Barrett's Esophagus: A Systematic Review and Meta-Analysis. (2009) Clin Gastroenterol Hepatol.

21. Galipeau, P C, Li, X, Blount, P L, et al., NSAIDs modulate CDKN2A, TP53, and DNA content risk for progression to esophageal adenocarcinoma. (2007) PLoS Med 4(2), e67.
22. Chao, D L, Sanchez, C A, Galipeau, P C, et al., Cell Proliferation, Cell Cycle Abnormalities, and Cancer Outcome in Patients with Barrett's Esophagus: A Long-term Prospective Study. (2008) Clin Cancer Res 14(21), 6988-6995.
23. Dunn, J M, Rabinovitch, P S, Oukrif, D, et al., Comparison of image cytometry and flow cytometry for detection of DNA ploidy abnormalities in Barrett's oesophagus. (2009) Biochemical Society Transactions In press.
24. Fang, M, Lew, E, Klein, M, et al., DNA abnormalities as marker of risk for progression of Barrett's esophagus to adenocarcinoma: image cytometric DNA analysis in formalin-fixed tissues. (2004) Am J Gastroenterol 99(10), 1887-1894.
25. Murray, L, Sedo, A, Scott, M, et al., TP53 and progression from Barrett's metaplasia to oesophageal adenocarcinoma in a UK population cohort. (2006) Gut 55(10), 1390-1397.
26. Lao-Sirieix, P, Lovat, L, and Fitzgerald, R C, Cyclin A immunocytology as a risk stratification tool for Barrett's esophagus surveillance. (2007) Clin Cancer Res 13(2 Pt 1), 659-665.
27. Jin, Z, Cheng, Y, Gu, W, et al., A Multicenter, Double-Blinded Validation Study of Methylation Biomarkers for Progression Prediction in Barrett's Esophagus. (2009) Cancer Res 69(10), 4112-4115.
28. Schulmann, K, Sterian, A, Berki, A, et al., Inactivation of p16, RUNX3, and HPP1 occurs early in Barrett's-associated neoplastic progression and predicts progression risk. (2005) Oncogene 24(25), 4138-4148.
29. R. Jones, K C I W, The Gastro-oesophageal Reflux Disease Impact Scale: a patient management tool for primary care. (2007) Alimentary Pharmacology & Therapeutics 25(12), 1451-1459.
30. Schlemper, R J, Riddell, R H, Kato, Y, et al., The Vienna classification of gastrointestinal epithelial neoplasia. (2000) Gut 47(2), 251-255.
31. NICE, Guide to the methods of technology appraisal. (2008) http://www.nice.org.uk/media/4A6/0F/SelectedFurtherReading210708.pdf.
32. Barbiere, J and Lyratzopoulos, G, Cost-Effectiveness of Endoscopic Screening Followed by Surveillance for Barrett's Esophagus: A Review. (2009) Gastroenterology.

TABLE 1 microarray datasets selected for analysis

| | Specimens | Array | Reference | Normalisation | Source of data |
|---|---|---|---|---|---|
| Hao, 2006[33] | 15 Normal oesophagus 14 Barrett's oesophagus | Spotted cDNA array (42,000 spots) | Commercial human RNA | Intensity-dependent | Stanford microarray database (http://genome-www5.stanford.edu) |
| Boussioutas, 2003[34] | 8 Normal stomach 27 Chronic gastritis 22 Gastric IM | Spotted cDNA array (11,500 spots) | Pool of 11 normal gastric specimen | LOWESS normalisation | GEO Accession GSE2669 |
| Greenawalt, 2007[35] | 39 Normal oesophagus 26 Barrett's oesophagus | Spotted cDNA array (11,500 spots) | Pool of 11 cell lines | LOWESS normalisation | ArrayExpress ID E-MEXP-692 |

TABLE 2

Clinical characteristics of cohorts

| | Number of patients | Age (median [95% CI]) | M:F ratio | Length BE (cm [95% CI]) |
|---|---|---|---|---|
| Real time PCR | | | | |
| Normal oesophagus | 10 | 62 [56-59] | 1.5:1 | 8.3 [6-10]* |
| Barrett's oesophagus | 10 | 65 [61-68] | 2:1 | |
| Gastric mucosa | 10 | 63 [56-69] | 1.5:1 | |
| Immunohistochemistry | | | | |
| Normal oesophagus | 20 | 59 [49-71] | 0.8:1 | 4.3 [3.2-5.3] |
| Barrett's oesophagus | 21 | 70 [63-78] | 2:1 | |
| Gastric mucosa | 24 | 62 [57-66] | 1.5:1 | |
| Duodenum | 18 | 58 [24-75] | 1:1 | |
| Capsule sponge | | | | |
| Control patients | 99 | 60 [58-62] | 1:1 | 5.7 [4.3-7.1] |
| Known Barrett's | 29 | 64 [60-67] | 3:1 | |

*indicate that the length of the BE samples used for RT-PCR is statistically longer than those for immunohistochemistry (p < 0.01)

TABLE 3

Putative biomarkers, primer sequences and PCR conditions

| Name | Symbol | Accession number | Forward primer | Reverse primer | Annealing T° C. |
|---|---|---|---|---|---|
| Anterior gradient 2 | AGR2 | NM_006408 | TTGTCCTCCTCAATCTGGTTTATG (SEQ ID NO. 1) | GCAGGTTCGTAAGCATAGAGAC (SEQ ID NO. 2) | 53 |
| ATPase, Cu2+ transporting, β polypeptide | ATP7B | NM_000053.2 | ACAAAGCACTAACCCAAAGAGAC (SEQ ID NO. 3) | ATATTCAAGACGCAAGACTTACAATG (SEQ ID NO. 4) | 53 |
| Death-associated protein kinase-1 | DAPK1 | NM_004938 | AACTACGAATTTGAGGATGAATACTTC (SEQ ID NO. 5) | GATCCAGGGATGCTGCAAAC (SEQ ID NO. 6) | 53 |
| M-Dopa decarboxylase | DDC | NM_000790 | CTTCGCCTACTTCCCCACTG (SEQ ID NO. 7) | CTTTGGTAGTTCCAGCATCTTCC (SEQ ID NO. 8) | 55 |
| Fructose-1,6-biphosphate decarboxylase | FBP 1 | NM_000507 | CACTGAGTACATCCAGAGGAAG (SEQ ID NO. 9) | CTTCTTGTTAGCGGGGTACAG (SEQ ID NO. 10) | 57 |
| Flavin containing monooxygenase | FMO5 | NM001461.1 | GGACAGGCGACACTAACAGG (SEQ ID NO. 11) | CCTTTCAAAGCAGACAGGTTCC (SEQ ID NO. 12) | 53 |
| Forkhead box A3 | FOXA3 | NM_004497.2 | TGCTGCCTCGACCACCAC (SEQ ID NO. 13) | AGTGAAATAGGGTGTGGAGGAAG (SEQ ID NO. 14) | 56 |
| Fucosyl-transferase 4 | FUT4 | NM_002033.2 | N/A* | N/A* | N/A |
| golgi phosphoprotein 2 | GOLPH2 | NM_177937.1 | AGTGTGAGGAGCGAATAGAAGAG (SEQ ID NO. 15) | TGTCTGGGACTTGCTGTTACC (SEQ ID NO. 16) | 53 |
| lysozyme (renal amyloidosis) | LYZ | NM_000239.1 | GACCTAGCAGTCAACATGAAGG (SEQ ID NO. 17) | CCATTCCCAATCTTTTCAGAGTTC (SEQ ID NO. 18) | 53 |
| phospholipase C-like 2 | PLCL2 | NM_015184.2 | CCATCAAGGAAGTGAGAACAGG (SEQ ID NO. 19) | ATATATGACGGAAAACGCACAATC (SEQ ID NO. 20) | 56 |
| ribonuclease, RNase A family, 4 | RNAse4 | NM_194430 | GCAGAGGACCCATTCATTGC (SEQ ID NO. 21) | CGCAGGAATCGCTGGTAC (SEQ ID NO. 22) | 57 |
| Trefoil factor 1 | TFF1 | NM 003225 | CCCCGTGAAAGACAGAATTGTG (SEQ ID NO. 23) | CGTCGATGGTATTAGGATAGAAGC (SEQ ID NO. 24) | 53 |
| Trefoil factor 3 | TFF3 | NM_003226.2 | TCTGGGAGCTTGACAAAGGC (SEQ ID NO. 25) | GGATTGTTTGCTTGGGGAAGG (SEQ ID NO. 26) | 56 |

The invention claimed is:

1. A non-endoscopic method of screening for Barrett's esophagus (BE) in a subject comprising:
   obtaining a sample of cells, including columnar mucosa cells and specialized columnar mucosa cells, from the subject by retrieving a swallowable device from the subject that has been swallowed by the subject, the swallowable device comprising an abrasive material configured to collect at least some columnar mucosa cells and at least some specialized columnar mucosa cells in the sample of cells;
   detecting a biomarker in the specialized columnar mucosa cells in the sample of cells; and
   differentiating between the columnar mucosa cells and the specialized columnar mucosa cells in the sample of cells by detecting the presence of the biomarker in the specialized columnar mucosa cells, wherein the biomarker is absent and not detected in the columnar mucosa cells; and wherein the biomarker is present and detected in the specialized columnar mucosa cells; thereby providing non-endoscopic screening for BE.

2. The method of claim 1, wherein the specialized columnar mucosa cells are esophageal cells.

3. The method of claim 2, wherein detecting the biomarker in esophageal specialized columnar mucosa cells is indicative of the subject having BE.

4. The method of claim 1, wherein the columnar mucosa cells are gastric cells.

5. The method of claim 1, wherein the biomarker is Trefoil factor 3 (TFF3).

6. The method of claim 5, wherein detecting TFF3 comprises detecting an antibody that specifically binds to TFF3 in an immunoassay of the sample of cells.

7. The method of claim 6, further comprising:
   differentiating between the columnar mucosa cells and the specialized columnar mucosa cells in the sample of cells by detecting the antibody that specifically binds to TFF3 in the specialized columnar mucosa cells.

8. The method of claim 5, wherein detecting TFF3 comprises immunohistochemically staining the sample of cells.

9. The method of claim 8, further comprising:
   differentiating between the columnar mucosa cells and the specialized columnar mucosa cells in the sample of cells by detecting TFF3 in the specialized columnar mucosa cells.

10. The method of claim 1, wherein the subject does not present with BE lesions.

11. The method of claim 1, wherein the swallowable device comprises a capsule sponge.

12. The method of claim 1, wherein the specificity and sensitivity of the method of screening for BE are about 80% and about 65% respectively.

13. The method of claim 1, wherein the specificity and sensitivity of the method of screening for BE are about 94% and about 78% respectively.

14. The method of claim 1, further comprising staining the sample of cells with an Alcian Blue stain to confirm diagnosis of BE.

15. The method of claim 1, wherein the abrasive material comprises polyurethane.

16. The method of claim 1, wherein the size and abrasiveness of the material is configured to sample substantially the entire esophageal surface of the subject.

17. The method of claim 1, wherein the abrasive material of the swallowable device is digestible.

18. The method of claim 17, further comprising a digestible retrieval cord coupled with the abrasive material, wherein the retrieval cord is configured to digest at a slower rate than the abrasive material.

* * * * *

SEQUENCE LISTING

<160> NUMBER OF SEQ ID NOS: 26

<210> SEQ ID NO 1
<211> LENGTH: 24
<212> TYPE: DNA
<213> ORGANISM: Artificial Sequence
<220> FEATURE:
<223> OTHER INFORMATION: Synthetic - Anterior gradient 2 forward primer

<400> SEQUENCE: 1
ttgtcctcct caatctggtt tatg                                           24

<210> SEQ ID NO 2
<211> LENGTH: 22
<212> TYPE: DNA
<213> ORGANISM: Artificial Sequence
<220> FEATURE:
<223> OTHER INFORMATION: Synthetic - Anterior gradient 2 reverse primer

<400> SEQUENCE: 2
gcaggttcgt aagcatagag ac    22

<210> SEQ ID NO 3
<211> LENGTH: 23
<212> TYPE: DNA
<213> ORGANISM: Artificial Sequence
<220> FEATURE:
<223> OTHER INFORMATION: Synthetic - ATPase, Cu2+ transporting, beta
      polypeptide forward primer

<400> SEQUENCE: 3
acaaagcact aacccaaaga gac    23

<210> SEQ ID NO 4
<211> LENGTH: 26
<212> TYPE: DNA
<213> ORGANISM: Artificial Sequence
<220> FEATURE:
<223> OTHER INFORMATION: Synthetic - ATPase, Cu2+ transporting, beta
      polypeptide reverse primer

<400> SEQUENCE: 4
atattcaaga cgcaagactt acaatg    26

<210> SEQ ID NO 5
<211> LENGTH: 27
<212> TYPE: DNA
<213> ORGANISM: Artificial Sequence
<220> FEATURE:
<223> OTHER INFORMATION: Synthetic - Death-associated protein kinase-1
      forward primer

<400> SEQUENCE: 5
aactacgaat tgaggatga atacttc    27

<210> SEQ ID NO 6
<211> LENGTH: 20
<212> TYPE: DNA
<213> ORGANISM: Artificial Sequence
<220> FEATURE:
<223> OTHER INFORMATION: Synthetic - Death-associated protein kinase-1
      reverse primer

<400> SEQUENCE: 6
gatccaggga tgctgcaaac    20

<210> SEQ ID NO 7
<211> LENGTH: 20
<212> TYPE: DNA
<213> ORGANISM: Artificial Sequence
<220> FEATURE:
<223> OTHER INFORMATION: Synthetic - M-Dopa decarboxylase forward primer

<400> SEQUENCE: 7
cttcgcctac ttccccactg    20

<210> SEQ ID NO 8

```
<211> LENGTH: 23
<212> TYPE: DNA
<213> ORGANISM: Artificial Sequence
<220> FEATURE:
<223> OTHER INFORMATION: Synthetic - M-Dopa decarboxylase reverse primer

<400> SEQUENCE: 8
ctttggtagt tccagcatct tcc                                              23

<210> SEQ ID NO 9
<211> LENGTH: 22
<212> TYPE: DNA
<213> ORGANISM: Artificial Sequence
<220> FEATURE:
<223> OTHER INFORMATION: Synthetic - Fructose-1,6-biphosphate
      decarboxylase forward primer

<400> SEQUENCE: 9
cactgagtac atccagagga ag                                               22

<210> SEQ ID NO 10
<211> LENGTH: 21
<212> TYPE: DNA
<213> ORGANISM: Artificial Sequence
<220> FEATURE:
<223> OTHER INFORMATION: Synthetic - Fructose-1,6-biphosphate
      decarboxylase reverse primer

<400> SEQUENCE: 10
cttcttgtta gcggggtaca g                                                21

<210> SEQ ID NO 11
<211> LENGTH: 20
<212> TYPE: DNA
<213> ORGANISM: Artificial Sequence
<220> FEATURE:
<223> OTHER INFORMATION: Synthetic - Flavin containing monooxygenase
      forward primer

<400> SEQUENCE: 11
ggacaggcga cactaacagg                                                  20

<210> SEQ ID NO 12
<211> LENGTH: 22
<212> TYPE: DNA
<213> ORGANISM: Artificial Sequence
<220> FEATURE:
<223> OTHER INFORMATION: Synthetic - Flavin containing monooxygenase
      reverse primer

<400> SEQUENCE: 12
cctttcaaag cagacaggtt cc                                               22

<210> SEQ ID NO 13
<211> LENGTH: 18
<212> TYPE: DNA
<213> ORGANISM: Artificial Sequence
<220> FEATURE:
<223> OTHER INFORMATION: Synthetic - Forkhead box A3 forward primer

<400> SEQUENCE: 13
tgctgcctcg accaccac                                                    18

<210> SEQ ID NO 14
<211> LENGTH: 23
<212> TYPE: DNA
<213> ORGANISM: Artificial Sequence
```

<220> FEATURE:
<223> OTHER INFORMATION: Synthetic - Forkhead box A3 reverse primer

<400> SEQUENCE: 14
agtgaaatag ggtgtggagg aag                                           23

<210> SEQ ID NO 15
<211> LENGTH: 23
<212> TYPE: DNA
<213> ORGANISM: Artificial Sequence
<220> FEATURE:
<223> OTHER INFORMATION: Synthetic - golgi phosphoprotein 2 forward
      primer

<400> SEQUENCE: 15
agtgtgagga gcgaatagaa gag                                           23

<210> SEQ ID NO 16
<211> LENGTH: 21
<212> TYPE: DNA
<213> ORGANISM: Artificial Sequence
<220> FEATURE:
<223> OTHER INFORMATION: Synthetic - golgi phosphoprotein 2 reverse
      primer

<400> SEQUENCE: 16
tgtctgggac ttgctgttac c                                             21

<210> SEQ ID NO 17
<211> LENGTH: 22
<212> TYPE: DNA
<213> ORGANISM: Artificial Sequence
<220> FEATURE:
<223> OTHER INFORMATION: Synthetic - lysozyme (renal amyloidosis)
      forward primer

<400> SEQUENCE: 17
gacctagcag tcaacatgaa gg                                            22

<210> SEQ ID NO 18
<211> LENGTH: 24
<212> TYPE: DNA
<213> ORGANISM: Artificial Sequence
<220> FEATURE:
<223> OTHER INFORMATION: Synthetic - lysozyme (renal amyloidosis)
      reverse primer

<400> SEQUENCE: 18
ccattcccaa tcttttcaga gttc                                          24

<210> SEQ ID NO 19
<211> LENGTH: 22
<212> TYPE: DNA
<213> ORGANISM: Artificial Sequence
<220> FEATURE:
<223> OTHER INFORMATION: Synthetic - phospholipase C-like 2 forward
      primer

<400> SEQUENCE: 19
ccatcaagga agtgagaaca gg                                            22

<210> SEQ ID NO 20
<211> LENGTH: 24
<212> TYPE: DNA
<213> ORGANISM: Artificial Sequence
<220> FEATURE:
<223> OTHER INFORMATION: Synthetic - phospholipase C-like 2 reverse primer

<400> SEQUENCE: 20
atatatgacg gaaaacgcac aatc                                          24

<210> SEQ ID NO 21
<211> LENGTH: 20
<212> TYPE: DNA
<213> ORGANISM: Artificial Sequence
<220> FEATURE:
<223> OTHER INFORMATION: Synthetic - ribonuclease, RNase A family, 4
      forward primer

<400> SEQUENCE: 21
gcagaggacc cattcattgc                                               20

<210> SEQ ID NO 22
<211> LENGTH: 18
<212> TYPE: DNA
<213> ORGANISM: Artificial Sequence
<220> FEATURE:
<223> OTHER INFORMATION: Synthetic - ribonuclease, RNase A family, 4
      reverse primer

<400> SEQUENCE: 22
cgcaggaatc gctggtac                                                 18

<210> SEQ ID NO 23
<211> LENGTH: 22
<212> TYPE: DNA
<213> ORGANISM: Artificial Sequence
<220> FEATURE:
<223> OTHER INFORMATION: Synthetic - Trefoil factor 1 forward primer

<400> SEQUENCE: 23
ccccgtgaaa gacagaattg tg                                            22

<210> SEQ ID NO 24
<211> LENGTH: 24
<212> TYPE: DNA
<213> ORGANISM: Artificial Sequence
<220> FEATURE:
<223> OTHER INFORMATION: Synthetic - Trefoil factor 1 reverse primer

<400> SEQUENCE: 24
cgtcgatggt attaggatag aagc                                          24

<210> SEQ ID NO 25
<211> LENGTH: 20
<212> TYPE: DNA
<213> ORGANISM: Artificial Sequence
<220> FEATURE:
<223> OTHER INFORMATION: Synthetic - Trefoil factor 3 forward primer

<400> SEQUENCE: 25
tctgggagct tgacaaaggc                                               20

<210> SEQ ID NO 26
<211> LENGTH: 21
<212> TYPE: DNA

```
<213> ORGANISM: Artificial Sequence
<220> FEATURE:
<223> OTHER INFORMATION: Synthetic - Trefoil factor 3 reverse primer

<400> SEQUENCE: 26
ggattgtttg cttggggaag g                                              21
```